United States Patent
Kurukchi et al.

(10) Patent No.: US 8,436,220 B2
(45) Date of Patent: May 7, 2013

(54) PROCESSES AND SYSTEMS FOR DEMETHANIZATION OF BROMINATED HYDROCARBONS

(75) Inventors: Sabah A. Kurukchi, Houston, TX (US); Yijun Liu, Houston, TX (US); Anand Moodley, Houston, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 0 days.

(21) Appl. No.: 13/157,584

(22) Filed: Jun. 10, 2011

(65) Prior Publication Data

US 2012/0313034 A1   Dec. 13, 2012

(51) Int. Cl.
*C07C 2/88* (2006.01)

(52) U.S. Cl.
USPC ........... 585/310; 585/943; 585/408; 585/469; 585/733

(58) Field of Classification Search .................. None
See application file for complete search history.

(56) References Cited

U.S. PATENT DOCUMENTS

| | | | |
|---|---|---|---|
| 2,168,260 A | 8/1939 | Heisel et al. | |
| 2,246,082 A | 6/1941 | Vaughan et al. | |
| 2,320,257 A | 5/1943 | Beekhuis | |
| 2,488,083 A * | 11/1949 | Gorin et al. | 585/642 |
| 2,536,457 A | 1/1951 | Mugdan | |
| 2,666,024 A | 1/1954 | Low et al. | |
| 2,677,598 A | 5/1954 | Crummett et al. | |
| 2,941,014 A | 6/1960 | Rothweiler et al. | |
| 3,076,784 A | 2/1963 | Schulte-Huemann et al. | |
| 3,172,915 A | 3/1965 | Borkowski et al. | |
| 3,246,043 A | 4/1966 | Rosset et al. | |
| 3,254,023 A | 5/1966 | Miale et al. | |
| 3,273,964 A | 9/1966 | Rosset | |
| 3,291,708 A | 12/1966 | Juda | |
| 3,294,846 A | 12/1966 | Livak et al. | |
| 3,310,380 A | 3/1967 | Lester | |
| 3,314,762 A | 4/1967 | Hahn | |
| 3,346,340 A | 10/1967 | Louvar et al. | |
| 3,353,916 A | 11/1967 | Lester | |
| 3,353,919 A | 11/1967 | Stockman | |
| 3,379,506 A | 4/1968 | Massonne et al. | |
| 3,468,968 A | 9/1969 | Baker et al. | |
| 3,496,242 A | 2/1970 | Berkowitz et al. | |
| 3,562,321 A | 2/1971 | Borkowski et al. | |
| 3,598,876 A | 8/1971 | Bloch | |

(Continued)

FOREIGN PATENT DOCUMENTS

| | | |
|---|---|---|
| CA | 1099656 | 4/1981 |
| CA | 1101441 | 5/1981 |

(Continued)

OTHER PUBLICATIONS

U.S. Appl. No. 60/487,364, filed Jul. 15, 2003, Lorkovic et al.

(Continued)

*Primary Examiner* — Tam M Nguyen
(74) *Attorney, Agent, or Firm* — Jack E. Ebel; Corey S. Tumey; Rodney F. Brown

(57) ABSTRACT

Process and systems for converting lower molecular weight alkanes to higher molecular weight hydrocarbons that include demethanization of brominated hydrocarbons, wherein the brominated hydrocarbons are formed by reaction of the lower molecular weight alkanes with bromine.

35 Claims, 8 Drawing Sheets

U.S. PATENT DOCUMENTS

| | | |
|---|---|---|
| 3,615,265 A | 10/1971 | Gartner |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |

| Patent | Date | Inventor |
|---|---|---|
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaefing |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |

| Patent No. | Date | Inventor(s) |
|---|---|---|
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller et al. |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |

| Patent | | Date | Inventor |
|---|---|---|---|
| 6,616,830 | B2 | 9/2003 | Elomari |
| 6,620,757 | B2 | 9/2003 | McConville et al. |
| 6,627,777 | B2 | 9/2003 | Rossi et al. |
| 6,632,971 | B2 | 10/2003 | Brown et al. |
| 6,635,793 | B2 | 10/2003 | Mul et al. |
| 6,641,644 | B2 | 11/2003 | Jagger et al. |
| 6,646,102 | B2 | 11/2003 | Boriack et al. |
| 6,669,846 | B2 | 12/2003 | Perriello |
| 6,672,572 | B2 | 1/2004 | Werlen |
| 6,679,986 | B1 | 1/2004 | Da Silva et al. |
| 6,680,415 | B1 | 1/2004 | Gulotty, Jr. et al. |
| 6,692,626 | B2 | 2/2004 | Keefer et al. |
| 6,692,723 | B2 | 2/2004 | Rouleau et al. |
| 6,710,213 | B2 | 3/2004 | Aoki et al. |
| 6,713,087 | B2 | 3/2004 | Tracy et al. |
| 6,713,655 | B2 | 3/2004 | Yilmaz et al. |
| RE38,493 | E | 4/2004 | Keefer et al. |
| 6,723,808 | B2 | 4/2004 | Holtcamp |
| 6,727,400 | B2 | 4/2004 | Messier et al. |
| 6,740,146 | B2 | 5/2004 | Simonds |
| 6,753,390 | B2 | 6/2004 | Ehrman et al. |
| 6,765,120 | B2 | 7/2004 | Weber et al. |
| 6,797,845 | B1 | 9/2004 | Hickman et al. |
| 6,797,851 | B2 | 9/2004 | Martens et al. |
| 6,821,924 | B2 | 11/2004 | Gulotty, Jr. et al. |
| 6,822,123 | B2 | 11/2004 | Stauffer |
| 6,822,125 | B2 | 11/2004 | Lee et al. |
| 6,825,307 | B2 | 11/2004 | Goodall |
| 6,825,383 | B1 | 11/2004 | Dewkar et al. |
| 6,831,032 | B2 | 12/2004 | Spaether |
| 6,838,576 | B1 | 1/2005 | Wicki et al. |
| 6,841,063 | B2 | 1/2005 | Elomari |
| 6,852,896 | B2 | 2/2005 | Stauffer |
| 6,866,950 | B2 | 3/2005 | Connor et al. |
| 6,869,903 | B2 | 3/2005 | Matsunaga |
| 6,875,339 | B2 | 4/2005 | Rangarajan et al. |
| 6,878,853 | B2 | 4/2005 | Tanaka et al. |
| 6,888,013 | B2 | 5/2005 | Paparatto et al. |
| 6,900,363 | B2 | 5/2005 | Harth et al. |
| 6,902,602 | B2 | 6/2005 | Keefer et al. |
| 6,903,171 | B2 | 6/2005 | Rhodes et al. |
| 6,909,024 | B1 | 6/2005 | Jones et al. |
| 6,921,597 | B2 | 7/2005 | Keefer et al. |
| 6,933,417 | B1 | 8/2005 | Henley et al. |
| 6,946,566 | B2 | 9/2005 | Yaegashi et al. |
| 6,953,868 | B2 | 10/2005 | Boaen et al. |
| 6,953,870 | B2 | 10/2005 | Yan et al. |
| 6,953,873 | B2 | 10/2005 | Cortright et al. |
| 6,956,140 | B2 | 10/2005 | Ehrenfeld |
| 6,958,306 | B2 | 10/2005 | Holtcamp |
| 6,984,763 | B2 | 1/2006 | Schweizer et al. |
| 7,001,872 | B2 | 2/2006 | Pyecroft et al. |
| 7,002,050 | B2 | 2/2006 | Santiago Fernandez et al. |
| 7,011,811 | B2 | 3/2006 | Elomari |
| 7,019,182 | B2 | 3/2006 | Grosso |
| 7,026,145 | B2 | 4/2006 | Mizrahi et al. |
| 7,026,519 | B2 | 4/2006 | Santiago Fernandez et al. |
| 7,037,358 | B2 | 5/2006 | Babicki et al. |
| 7,045,670 | B2 | 5/2006 | Johnson et al. |
| 7,049,388 | B2 | 5/2006 | Boriack et al. |
| 7,053,252 | B2 | 5/2006 | Boussand et al. |
| 7,057,081 | B2 | 6/2006 | Allison et al. |
| 7,060,865 | B2 | 6/2006 | Ding et al. |
| 7,064,238 | B2 | 6/2006 | Waycuilis |
| 7,064,240 | B2 | 6/2006 | Ohno et al. |
| 7,067,448 | B1 | 6/2006 | Weitkamp et al. |
| 7,083,714 | B2 | 8/2006 | Elomari |
| 7,084,308 | B1 | 8/2006 | Stauffer |
| 7,091,270 | B2 | 8/2006 | Zilberman et al. |
| 7,091,387 | B2 | 8/2006 | Fong et al. |
| 7,091,391 | B2 | 8/2006 | Stauffer |
| 7,094,936 | B1 | 8/2006 | Owens et al. |
| 7,098,371 | B2 | 8/2006 | Mack et al. |
| 7,105,710 | B2 | 9/2006 | Boons et al. |
| 7,138,534 | B2 | 11/2006 | Forlin et al. |
| 7,141,708 | B2 | 11/2006 | Marsella et al. |
| 7,145,045 | B2 | 12/2006 | Harmsen et al. |
| 7,148,356 | B2 | 12/2006 | Smith, III et al. |
| 7,148,390 | B2 | 12/2006 | Zhou et al. |
| 7,151,199 | B2 | 12/2006 | Martens et al. |
| 7,161,050 | B2 | 1/2007 | Sherman et al. |
| 7,169,730 | B2 | 1/2007 | Ma et al. |
| 7,176,340 | B2 | 2/2007 | Van Broekhoven et al. |
| 7,176,342 | B2 | 2/2007 | Bellussi et al. |
| 7,182,871 | B2 | 2/2007 | Perriello |
| 7,193,093 | B2 | 3/2007 | Murray et al. |
| 7,196,239 | B2 | 3/2007 | Van Egmond et al. |
| 7,199,083 | B2 | 4/2007 | Zevallos |
| 7,199,255 | B2 | 4/2007 | Murray et al. |
| 7,208,641 | B2 | 4/2007 | Nagasaki et al. |
| 7,214,750 | B2 | 5/2007 | McDonald et al. |
| 7,220,391 | B1 | 5/2007 | Huang et al. |
| 7,226,569 | B2 | 6/2007 | Elomari |
| 7,226,576 | B2 | 6/2007 | Elomari |
| 7,230,150 | B2 | 6/2007 | Grosso et al. |
| 7,230,151 | B2 | 6/2007 | Martens et al. |
| 7,232,872 | B2 | 6/2007 | Shaffer et al. |
| 7,238,846 | B2 | 7/2007 | Janssen et al. |
| 7,244,795 | B2 | 7/2007 | Agapiou et al. |
| 7,244,867 | B2 | 7/2007 | Waycuilis |
| 7,250,107 | B2 | 7/2007 | Benazzi et al. |
| 7,250,542 | B2 | 7/2007 | Smith, Jr. et al. |
| 7,252,920 | B2 | 8/2007 | Kurokawa et al. |
| 7,253,327 | B2 | 8/2007 | Janssens et al. |
| 7,253,328 | B2 | 8/2007 | Stauffer |
| 7,265,193 | B2 | 9/2007 | Weng et al. |
| 7,267,758 | B2 | 9/2007 | Benazzi et al. |
| 7,268,263 | B1 | 9/2007 | Frey et al. |
| 7,271,303 | B1 | 9/2007 | Sechrist et al. |
| 7,273,957 | B2 | 9/2007 | Bakshi et al. |
| 7,282,603 | B2 | 10/2007 | Richards |
| 7,285,698 | B2 | 10/2007 | Liu et al. |
| 7,304,193 | B1 | 12/2007 | Frey et al. |
| 7,342,144 | B2 | 3/2008 | Kaizik et al. |
| 7,348,295 | B2 | 3/2008 | Zones et al. |
| 7,348,464 | B2 | 3/2008 | Waycuilis |
| 7,357,904 | B2 | 4/2008 | Zones et al. |
| 7,361,794 | B2 | 4/2008 | Grosso |
| 7,365,102 | B1 | 4/2008 | Weissman |
| 7,390,395 | B2 | 6/2008 | Elomari |
| 7,560,607 | B2 | 7/2009 | Waycuilis |
| 7,674,941 | B2 | 3/2010 | Waycuilis et al. |
| 7,713,510 | B2 | 5/2010 | Harrod et al. |
| 7,880,041 | B2 | 2/2011 | Waycuilis |
| 8,008,535 | B2 | 8/2011 | Waycuilis |
| 8,173,851 | B2 | 5/2012 | Waycuilis et al. |
| 8,198,495 | B2 | 6/2012 | Waycuilis et al. |
| 8,232,441 | B2 | 7/2012 | Waycuilis |
| 8,282,810 | B2 | 10/2012 | Waycuilis |
| 8,367,884 | B2 | 2/2013 | Waycuilis |
| 2002/0102672 | A1 | 8/2002 | Mizrahi |
| 2002/0193649 | A1 | 12/2002 | O'Rear et al. |
| 2002/0198416 | A1 | 12/2002 | Zhou et al. |
| 2003/0004380 | A1 | 1/2003 | Grumann |
| 2003/0065239 | A1 | 4/2003 | Zhu |
| 2003/0069452 | A1 | 4/2003 | Sherman et al. |
| 2003/0078456 | A1 | 4/2003 | Yilmaz et al. |
| 2003/0120121 | A1 | 6/2003 | Sherman et al. |
| 2003/0125589 | A1 | 7/2003 | Grosso |
| 2003/0166973 | A1 | 9/2003 | Zhou et al. |
| 2004/0006246 | A1 | 1/2004 | Sherman et al. |
| 2004/0062705 | A1 | 4/2004 | Leduc |
| 2004/0152929 | A1 | 8/2004 | Clarke |
| 2004/0158107 | A1 | 8/2004 | Aoki |
| 2004/0158108 | A1 | 8/2004 | Snoble |
| 2004/0171779 | A1 | 9/2004 | Matyjaszewski et al. |
| 2004/0187684 | A1 | 9/2004 | Elomari |
| 2004/0188271 | A1 | 9/2004 | Ramachandraiah et al. |
| 2004/0188324 | A1 | 9/2004 | Elomari |
| 2004/0220433 | A1 | 11/2004 | Van Der Heide |
| 2005/0027084 | A1 | 2/2005 | Clarke |
| 2005/0038310 | A1 | 2/2005 | Lorkovic et al. |
| 2005/0042159 | A1 | 2/2005 | Elomari |
| 2005/0047927 | A1 | 3/2005 | Lee et al. |
| 2005/0148805 | A1 | 7/2005 | Jones |
| 2005/0171393 | A1 | 8/2005 | Lorkovic |
| 2005/0192468 | A1 | 9/2005 | Sherman et al. |
| 2005/0215837 | A1 | 9/2005 | Hoffpauir |

| Pub. No. | Date | Name | | Country | Number | Date |
|---|---|---|---|---|---|---|
| 2005/0218041 A1 | 10/2005 | Yoshida et al. | | EP | 0418974 A1 | 3/1991 |
| 2005/0234276 A1 | 10/2005 | Waycuilis | | EP | 0418975 A1 | 3/1991 |
| 2005/0234277 A1 | 10/2005 | Waycuilis | | EP | 0510238 A1 | 10/1992 |
| 2005/0245771 A1 | 11/2005 | Fong et al. | | EP | 0526908 A2 | 2/1993 |
| 2005/0245772 A1 | 11/2005 | Fong | | EP | 0346612 B1 | 8/1993 |
| 2005/0245777 A1 | 11/2005 | Fong | | EP | 0560546 A1 | 9/1993 |
| 2005/0267224 A1 | 12/2005 | Herling | | EP | 0976705 A1 | 2/2000 |
| 2006/0025617 A1 | 2/2006 | Begley | | EP | 1186591 A2 | 3/2002 |
| 2006/0100469 A1 | 5/2006 | Waycuilis | | EP | 1253126 A1 | 10/2002 |
| 2006/0135823 A1 | 6/2006 | Jun | | EP | 1312411 A2 | 5/2003 |
| 2006/0138025 A1 | 6/2006 | Zones | | EP | 1235769 B1 | 5/2004 |
| 2006/0138026 A1 | 6/2006 | Chen | | EP | 1435349 A2 | 7/2004 |
| 2006/0149116 A1 | 7/2006 | Slaugh | | EP | 1440939 A1 | 7/2004 |
| 2006/0229228 A1 | 10/2006 | Komon et al. | | EP | 1235772 B1 | 1/2005 |
| 2006/0229475 A1 | 10/2006 | Weiss et al. | | EP | 1661620 A1 | 5/2006 |
| 2006/0270863 A1 | 11/2006 | Reiling | | EP | 1760057 A1 | 3/2007 |
| 2006/0288690 A1 | 12/2006 | Elomari | | EP | 1689728 B1 | 4/2007 |
| 2007/0004955 A1 | 1/2007 | Kay | | EP | 1808227 A1 | 7/2007 |
| 2007/0078285 A1 | 4/2007 | Dagle | | EP | 1837320 A1 | 9/2007 |
| 2007/0100189 A1 | 5/2007 | Stauffer | | GB | 5125 | 0/1912 |
| 2007/0129584 A1 | 6/2007 | Basset | | GB | 156122 | 3/1922 |
| 2007/0142680 A1 | 6/2007 | Ayoub | | GB | 294100 | 6/1929 |
| 2007/0148067 A1 | 6/2007 | Zones | | GB | 363009 | 12/1931 |
| 2007/0148086 A1 | 6/2007 | Zones | | GB | 402928 | 12/1933 |
| 2007/0149778 A1 | 6/2007 | Zones | | GB | 474922 A | 11/1937 |
| 2007/0149789 A1 | 6/2007 | Zones | | GB | 536491 | 5/1941 |
| 2007/0149819 A1 | 6/2007 | Zones | | GB | 553950 | 6/1943 |
| 2007/0149824 A1 | 6/2007 | Zones | | GB | 586483 | 3/1947 |
| 2007/0149837 A1 | 6/2007 | Zones | | GB | 775590 | 5/1957 |
| 2007/0149838 A1 | 6/2007 | Chretien | | GB | 793214 | 4/1958 |
| 2007/0197801 A1 | 8/2007 | Bolk | | GB | 796048 | 6/1958 |
| 2007/0197847 A1 | 8/2007 | Liu | | GB | 796085 | 6/1958 |
| 2007/0213545 A1 | 9/2007 | Bolk | | GB | 883256 A | 11/1961 |
| 2007/0238905 A1 | 10/2007 | Arredondo | | GB | 930341 A | 7/1963 |
| 2007/0238909 A1 | 10/2007 | Gadewar et al. | | GB | 950975 | 3/1964 |
| 2007/0276168 A1 | 11/2007 | Garel | | GB | 950976 | 3/1964 |
| 2007/0284284 A1 | 12/2007 | Zones | | GB | 991303 | 5/1965 |
| 2008/0022717 A1 | 1/2008 | Yoshida et al. | | GB | 995960 | 6/1965 |
| 2008/0152555 A1 | 6/2008 | Wang et al. | | GB | 1015033 | 12/1965 |
| 2008/0171898 A1 | 7/2008 | Waycuilis | | GB | 1104294 | 2/1968 |
| 2008/0183022 A1 | 7/2008 | Waycuilis | | GB | 1133752 | 11/1968 |
| 2008/0188697 A1 | 8/2008 | Lorkovic | | GB | 1172002 | 11/1969 |
| 2008/0200740 A1 | 8/2008 | Waycuilis | | GB | 1212240 | 11/1970 |
| 2008/0210596 A1 | 9/2008 | Litt et al. | | GB | 1233299 | 5/1971 |
| 2008/0275279 A1 | 11/2008 | Podkolzin et al. | | GB | 1253618 | 11/1971 |
| 2008/0275284 A1 | 11/2008 | Waycuilis | | GB | 1263806 | 2/1972 |
| 2008/0314758 A1* | 12/2008 | Grosso et al. .......... 205/431 | | GB | 1446803 | 8/1976 |
| 2009/0005620 A1 | 1/2009 | Waycuilis et al. | | GB | 1542112 | 3/1979 |
| 2009/0163749 A1 | 6/2009 | Li et al. | | GB | 2095243 A | 9/1982 |
| 2009/0247796 A1 | 10/2009 | Waycuilis et al. | | GB | 2095245 A | 9/1982 |
| 2009/0270655 A1 | 10/2009 | Fong et al. | | GB | 2095249 A | 9/1982 |
| 2009/0306443 A1 | 12/2009 | Stark et al. | | GB | 2116546 A | 9/1982 |
| 2009/0308759 A1 | 12/2009 | Waycuilis | | GB | 2120249 A | 11/1983 |
| 2009/0312586 A1 | 12/2009 | Waycuilis et al. | | GB | 2185754 A | 7/1987 |
| 2009/0326292 A1 | 12/2009 | Waycuilis | | GB | 2191214 A | 12/1987 |
| 2010/0030005 A1 | 2/2010 | Sauer et al. | | SU | 694483 A1 | 10/1979 |
| 2010/0087686 A1 | 4/2010 | Fong et al. | | WO | 83/00859 | 3/1983 |
| 2010/0096588 A1 | 4/2010 | Gadewar et al. | | WO | 85/04863 | 11/1985 |
| 2010/0099930 A1* | 4/2010 | Stoimenov et al. .......... 570/101 | | WO | 85/04867 | 11/1985 |
| 2010/0105972 A1 | 4/2010 | Lorkovic | | WO | 90/08120 | 7/1990 |
| 2010/0234637 A1 | 9/2010 | Fong et al. | | WO | 90/08752 | 8/1990 |
| 2010/0270167 A1* | 10/2010 | McFarland .......... 205/462 | | WO | 91/18856 | 12/1991 |
| 2011/0015458 A1 | 1/2011 | Waycuilis et al. | | WO | 92/03401 | 3/1992 |
| 2011/0071326 A1 | 3/2011 | Waycuilis | | WO | 92/12946 | 8/1992 |
| 2011/0218372 A1 | 9/2011 | Waycuilis et al. | | WO | 93/16798 | 9/1993 |
| 2011/0218374 A1 | 9/2011 | Waycuilis | | WO | 96/22263 | 7/1996 |
| 2012/0141356 A1 | 6/2012 | Bricket et al. | | WO | 97/44302 | 11/1997 |
| 2012/0245399 A1 | 9/2012 | Kurukchi et al. | | WO | 98/12165 | 3/1998 |
| 2013/0006024 A1 | 1/2013 | Kurukchi et al. | | WO | 99/07443 | 2/1999 |
| 2013/0046121 A1 | 2/2013 | Kurukchi et al. | | WO | 00/07718 A1 | 2/2000 |
| FOREIGN PATENT DOCUMENTS | | | | WO | 00/09261 A1 | 2/2000 |
| CA | 1202610 | 4/1986 | | WO | 01/14300 A1 | 3/2001 |
| CA | 2542857 | 5/2005 | | WO | 01/38275 A1 | 5/2001 |
| CA | 2236126 | 8/2006 | | WO | 01/44149 A1 | 6/2001 |
| CA | 2203115 | 9/2006 | | WO | 02/094749 A1 | 11/2002 |
| CA | 2510093 | 12/2006 | | WO | 02/094750 A1 | 11/2002 |
| EP | 0164798 A1 | 12/1985 | | WO | 02/094751 A2 | 11/2002 |
| EP | 0418971 A1 | 3/1991 | | WO | 02/094752 A1 | 11/2002 |
| | | | | WO | 03/000635 A1 | 1/2003 |

| | | |
|---|---|---|
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067183 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |
| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |
| WO | 2011/109244 A2 | 9/2011 |
| WO | 2011/159490 A1 | 12/2011 |
| WO | 2012/128922 A1 | 9/2012 |
| WO | 2012/170132 A1 | 12/2012 |
| WO | 2013/002888 A1 | 1/2013 |
| WO | 2013/025281 A1 | 2/2013 |

OTHER PUBLICATIONS

U.S. Appl. No. 60/559,844, filed Apr. 6, 2004, Sherman et al.
U.S. Appl. No. 60/765,115, filed Feb. 3, 2006, Gadewar et al.
U.S. Office Communication from U.S. Appl. No. 10/365,346 dated Jun. 12, 2006.
U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/502,024 dated Oct. 26, 2010.
U.S. Office Communication from U.S. Appl. No. 12/715,526 dated Feb. 17, 2011.
U.S. Office Communication from U.S. Appl. No. 12/139,135 dated Apr. 14, 2011.
U.S. Office Communication from U.S. Appl. No. 12/715,526 dated May 24, 2011.
U.S. Office Communication from U.S. Appl. No. 12/502,024 dated May 31, 2011.
U.S. Office Communication from U.S. Appl. No. 12/139,135 dated Oct. 14, 2011.
U.S. Office Communication from U.S. Appl. No. 12/477,307 dated Oct. 7, 2011.
U.S. Office Communication from U.S. Appl. No. 12/477,319 dated Jul. 22, 2011.
U.S. Office Communication from U.S. Appl. No. 12/502,024 dated Sep. 16, 2011.

U.S. Office Communication from U.S. Appl. No. 12/477,307 dated Feb. 27, 2012.
U.S. Office Communication from U.S. Appl. No. 12/715,526 dated Jan. 4, 2012.
Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.
Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999, Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.
Abstract of CN 1623969, Method for preparing 1, 4-benzene dimethanol, Publication date: Jun. 8, 2005, Inventor: Jiarong et al., esp@cenet database—worldwide.
Abstract of CN 1657592, Method for converting oil to multiple energy fuel product, Publication date: Aug. 24, 2005, Inventor: Li. esp@cenet database—worldwide.
Abstract of CN 1687316, Method for producing biologic diesel oil from rosin, Publication date: Oct. 26, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publication date: Dec. 7, 2005, Inventor: Gao, esp@cenet database—worldwide.
Abstract of CN 1724612, Biological diesel oil catalyst and method of synthesizing biological diesel oil using sai catalyst, Publication date: Jan. 25, 2006, Inventor: Gu, esp@cenet database—worldwide.
Abstract of CN 1986737, Process for producing biodiesel oil with catering waste oil, Publication date: Jun. 27, 2007, Inventor: Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.

Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.
Abstract of EP 0021497 (A1), Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Baltha sart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,-2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004-529189 (best available copy).
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.

Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@cenet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.
Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Ame et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.
Abstract of WO 2007137566, Method for catalytic conversion of organic oxygenated compounds from biomaterials, Publication date: Dec. 6, 2007, Inventor: Reschetilowski, esp@cenet database—worldwide.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.

Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobromic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.
Bradshaw et al., Production of hydrobromic acid from bromine and methane for hydrogen production, Proceedings of the 2001 DOE Hydrogen Program Review, NREL/CP-570-30535, 2001, pp. 1-8.
Chang et al., The conversion of methanol and other O-compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc., pp. 1-13.
Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.
Final Report, Abstract, http://chemelab.ucsd.edu/methanol/memos/final.html, May 9, 2004, pp. 1-7.
Gibson, Phase-transfer synthesis of monoalkyl ethers of oligoethylene glycols, J. Org. Chem. 1980, vol. 45, No. 6, pp. 1095-1098, XP002427776.
http://webbook.nist.gov/, Welcome to the NIST chemistry webbook, Sep. 10, 2007, U.S. Secretary of Commerce on Behalf of the United States of America, pp. 1-2.
Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.
Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.
JLM Technology Ltd., The Miller GLS Technology for conversation of light hydrocarbons to alcohols, New Science for the Benefit of Humanity, May 31, 2000; pp. 1-10.
Kirk-Othmer, Encyclopedia of Chemical Technology, 4th Edition, vol. 1, A Wiley-Interscience Publication, John Wiley & Sons, 1991, pp. 946-997.
Liu et al., Higher hydrocarbons from methane condensation mediated by HBr, Journal of Molecular Catalysis A: Chemical 273, Elsevier B.V., 2007, pp. 14-20.
Loiseau et al., Multigram synthesis of well-defined extended bifunctional polyethylene glycol (PEG) chains, J. Org. Chem., vol. 69, No. 3, XO-002345040, 2004, pp. 639-647.
Lorkovic et al., A novel integrated process for the functionalization of methane and ethane: bromine as mediator, Catalysis Today 98, 2004, pp. 317-322.
Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.
Lorkovic et al., C1 coupling via bromine activation and tandem catalytic condensation and neutralization over CaO/zeolite composites, Chem. Comm. 2004, pp. 566-567.
Mihai, et al., Application of Bronsted-type LFER in the study of the phospholipase C Mechanism, J. Am. Chem. Soc., vol. 125, No. 11, XP-002427777, 2003, pp. 3236-3242.
Mishakov et al., Nanocrystalline MgO as a dehydrohalogenation catalyst, Journal of Catalysis 206, Elsevier Science, USA, 2002, pp. 40-48.

Mochida, et al., The catalytic dehydrohalogenation of haloethanes on solid acids and bases, Bulletin of the Chemical Society of Japan, vol. 44, Dec. 1971, pp. 3305-3310.
Motupally et al., Recycling chlorine from hydrogen chloride, The Electrochemical Society Interface, Fall 1998, pp. 32-36.
Murray et al., Conversion of methyl halides to hydrocarbons on basic zeolites: a discovery by in situ NMR, J. Am. Chem. Soc., 1993, vol. 115, pp. 4732-4741.
Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.
Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.
Olah et al., Antimony pentafluoride/graphite catalyzed oxidative conversion of methyl halides with copper oxides (or copper/oxygen) to dimethyl ether, J. Org. Chem. 1990, 55, pp. 4289-4293.
Olah, Electrophilic methane conversion, American Chemical Society, Acc. Chem. Res. 1987, 20, pp. 422-428.
Olah, Hydrocarbons through methane derivatives, Hydrocarbon Chemistry, 1995, pp. 89-90, John Wiley & Sons, Inc.
Olah et al., Hydrocarbons through methane derivatives, Hydrocarbon Chemistry, 2nd Edition, 2003, pp. 123, 149, and 153, John Wiley & Sons, Inc.
Olah et al., Onium Ylide Chemistry. 1. Bifunctional acid-base-catalyzed conversion of heterosubstituted methanes into ethylene and derived hydrocarbons. The Onium Ylide mechanism of the C1-C2 conversion. J. Am. Chem. Soc. 1984, 106, pp. 2143-2149.
Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.
Prelog et al., 234. Chirale 2, 2'-polyoxaalkano-9,9'-spirobifluorene, Helvetica Chimica Acta, vol. 62, No. 7, 1979 pp. 2285-2302.
Rakoff et al., Quimica Organica Fundamental, Organic Chemistry, The Macmillan Company, 1966, pp. 58-63 and 76-77.
Richards, et al., Nanocrystalline ultra high surface area magnesium oxide as a selective base catalyst, Scripta Materialia, 44, 2001, pp. 1663-1666, Elsevier Science Ltd.
Shimizu et al., Gas-Phase electrolysis of hydrobromic acid using PTFE-bonded carbon electrode, Int. J. Hydrogen Energy, vol. 13, No. 6, pp. 345-349, 1988.
Smirnov et al., Selective bromination of alkanes and arylalkanes with CBr4, Mendeleev Commun., 2000, pp. 175-176.
Sun et al., Nanocrystal metal oxide—Chlorine adducts: selective catalysts for chlorination of alkanes, J. Am. Chem. Soc., 1999, 121, pp. 5587-5588.
Sun et al., A general integrated process for synthesizing olefin oxides, Chem. Commun., The Royal Society of Chemistry 2004, pp. 2100-2101.
Tamura et al., The reactions of grignard reagents with transition metal halides: Coupling, disproportionation, and exchange with olefins, Bulletin of the Chemical Society of Japan, vol. 44, Nov. 1971, pp. 3063-3073.
Taylor et al., Direct conversion of methane to liquid hydrocarbons through chlorocarbon intermediates, 1988, Elsevier Science Publishers B.V. Amsterdam, Netherlands, pp. 483-489.
Taylor, Conversion of substituted methanes over ZSM-catalysts, 2000, pp. 3633-3638, Studies in Surface Science and Catalysis 130, Elsevier Science B.V.
Taylor, PETC's on-site naural gas conversion efforts, Preprints of the Fuel Division, 208th National Meeting of the American Chemical Society, 39 (4), 1994, pp. 1228-1232.
Thomas et al., Catalytically active centres in porous oxides: design and performance of highly selective new catalysts, Chem. Commun., 2001, pp. 675-687.
Thomas et al., Synthesis and characterization of a catalytically active nickel-silicoaluminophosphate catalyst for the conversion of methanol to ethene, American Chemical Society, 1991, 3, pp. 667-672.

Van Velzen et al., HBr electrolysis in the Ispra mark 13A flue gas desulphurization process: electrolysis in a DEM cell, Journal of Applied Electrochemistry, 20, 1990, pp. 60-68.

Wagner et al., Reactions of VX, GD, and HD with nanosize CaO: autocatalytic dehydrohalogenation of HD, J. Phys. Chem. B 2000, 104, pp. 5118-5123, 2000 American Chemical Society.

Wauters et al., Electrolytic membrane recovery of bromine from waste hydrogen bromide streams, AIChE Journal, Oct. 1998, vol. 44, No. 10, pp. 2144-2148.

Weissermel et al., Industrial Organic Chemistry, 3rd Edition, 1997, pp. 160-162, and 208.

Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.

Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.

Zhou et al., An integrated process for partial oxidation of alkanes, Chem. Commun., 2003, The Royal Society of Chemistry, pp. 2294-2295.

ZSM-5 Catalyst, http://chemelba.ucsd.edu/methanol/memos/ZSM-5.html, Nov. 6, 2003, p. 1.

Abstract of GB 998681(A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al., http://www19.ipdl.inpit.go.jp/PA1/result . . . .

Hannus, Adsorption and transformation of halogenated hydrocarbons over zeolites, Applied Catalysis A: General 189, 1999, XP-002634422, pp. 263-276.

Howe, Zeolite catalysts for dehalogenation processes, Applied Catalysis A: General 271, 2004, XP-002634421, pp. 3-11.

Li et al., Pyrolysis of Halon 1301 over zeolite catalysts, Microporous and Mesoporous Materials 35-36, 2000, XP-002634423, pp. 219-226.

Chretien; Process for the Adjustment of the HHV in the LNG Plants; 23rd World Gas Conference; Amsterdam 2006; Jun. 5-9, 2006; pp. 1-14.

Yang et al.; Maximising the Value of Surplus Ethane and Cost-Effective Design to Handle Rich LNG; publ. date Jun. 1, 2007; pp. 1-13.

Henshuiinkai, Kagaku Daijiten; Kagaku Daijiten 4, Japan, Kyoritsu Publisher, Oct. 15, 1963; pp. 652-654.

Jacobson, C.A.; "Encyclopedia of Chemical Reactions"; vol. 1; 1946; pp. 722.

U.S. Office Communication from U.S. Appl. No. 12/957,036 dated Aug. 16, 2012.

U.S. Office Communication from U.S. Appl. No. 12/792,335 dated Aug. 17, 2012.

U.S. Office communication from U.S. Appl. No. 12/792,335 dated Jan. 2, 2013.

U.S. Office communication from U.S. Appl. No. 13/117,785 dated Mar. 14, 2013.

Abstract of JP publication No. 08-283182, Production of Hydrochloromethanes, Publication date Oct. 29, 1996, Inventor: Kojiro et al., http://www19.ipdl.inpit.go.jp.

* cited by examiner

PROCESSES AND SYSTEMS FOR DEMETHANIZATION OF BROMINATED HYDROCARBONS

BACKGROUND

The present invention relates generally to processes and systems for converting lower molecular weight alkanes to higher molecular weight hydrocarbons and, more particularly, in one or more embodiments, to processes for converting lower molecular weight alkanes that include demethanization of brominated hydrocarbons, wherein the brominated hydrocarbons are formed by reaction of the lower molecular weight alkanes with bromine.

Natural gas, which is primarily composed of methane and other light alkanes, has been discovered in large quantities throughout the world. In the United States, the latest proved natural gas reserves are 6,731 billion standard cubic meter (238 trillion standard cubic feet) in 2010, which makes the United States a top-five country in natural gas abundance. Natural gas is generally a cleaner energy source than crude oil. It is normally heavy sulfur-free and contains none or a minimum amount of heavy metals and non-reacting heavy hydrocarbons. For a given amount of heat energy, burning natural gas produces about half as much carbon dioxide as coal.

However, the transportation, storage and distribution of natural gas in a gaseous form are much less favorable than those of crude oil making it more difficult to be a substitute as the predominant energy source. Converting natural gas to higher molecular weight hydrocarbons which, due to their higher density and value, are able to be more economically transported can significantly aid the development of natural gas reserves, particularly the stranded remote natural gas reserves.

One technique for converting natural gas to higher molecular weight hydrocarbons is a bromine-based process. In general, the bromine-based process may include several basic steps, as listed below.

(1) Bromination: Reacting bromine with lower molecular weight alkanes to produce alkyl bromides and hydrogen bromide (HBr).
(2) Alkyl Bromide Conversion: Reacting the alkyl bromides over a suitable catalyst under sufficient conditions to produce HBr, methane (C1), light end hydrocarbons (C2-C4), and heavy end hydrocarbons (C5+).
(3) HBr Recovery: Recovering HBr produced in both steps (1) and (2) by one of several processes, e.g., absorbing HBr and neutralizing the resulting hydrobromic acid with an aqueous solution of partially oxidized metal bromide salts (as metal oxides/oxy-bromides/bromides) to produce metal bromide salt and water in an aqueous solution; reacting HBr with metal oxide; or absorbing HBr into water using a packed tower or other contacting device.
(4) Bromine Regeneration: Reacting the bromide recovered in step (3) with oxygen or air to yield bromine and treating it sufficiently for recycle to step (1).
(5) Product Recovery: Fractionating by distillation and cryogenic distillation (demethanizer) the hydrocarbon mixtures contained in the effluent from step (2) and then separated from HBr in step (3) into methane, light end hydrocarbons, and heavy end hydrocarbons. The methane stream can be compressed for recycle to step (1). The light end hydrocarbon (C2-C4) stream may be, for example, salable as a product or cracked to produce light olefins. The heavy end hydrocarbons (C5+) may be used, for example, for further petrochemical or fuel processing.

A simplified block diagram of an example process for converting natural gas to higher molecular weight hydrocarbons is illustrated in FIG. 1.

In the bromine-based processes, mono-brominated alkanes created during bromination may be desirable as the predominant reactant species for the subsequent alkyl bromide conversion. Poly-brominated alkanes are known to adversely affect the selectivity profiles of the higher molecular weight hydrocarbons produced during the alkyl bromide conversion and, more importantly, promote the formation of coke which can deposit on the catalyst, block the active sites, and cause rapid catalyst deactivation. The higher selectivity of poly-brominated alkanes can also lower the utilization efficiency of bromine, requiring a higher circulating flow of bromine which can correspond to a higher cost in recovering hydrogen bromide and regenerating recyclable bromine.

To achieve higher selectivity of mono-brominated alkanes and reduce the formation of bromination carbon/soot, a large excess of methane or large methane-to-bromine ratio can be used. In the case of the bromination of methane, a methane-to-bromine ratio of about 6:1 can be used to increase the selectivity to mono-bromomethane ($CH_3Br$) to average approximately 88% depending on other reaction conditions. If a lower methane-to-bromine ratio of approximately 2.6:1 is utilized, selectivity of $CH_3Br$ may fall to the range of approximately 65-75% depending, for example, on other reaction conditions. If a methane-to-bromine ratio significantly less than 2.5:1 is utilized, unacceptably low selectivity to $CH_3Br$ occurs, and, moreover, significant formation of undesirable di-bromomethane, tri-bromomethane, and carbon soot is observed. However, the large methane-to-bromine ratio can be problematic, in that the large excess methane represents a large recycle stream circulating throughout the entire system. For example, the pressure drop of the process gas between the feed to bromination in step (1) and the recycle methane from product recovery in the step (5) can be large, resulting in a high cost of compression for the recycle gas.

In alkyl bromide conversion, the exothermic coupling reaction may be carried out in a fixed-bed, fluidized-bed or other suitable reactor in the presence of suitable catalysts under sufficient conditions (e.g. 150-600° C., 1-80 bar). The catalyst may have to undergo decoking periodically or continuously to maintain adequate performance. In some instances, a fluidized-bed reactor may be considered to be advantageous for the coupling reaction, particularly for commercial scale of operation, as it should allow for continuous removal of coke and regeneration of the spent catalyst without requiring daily shutdowns and expensive cyclic operation. The fluidized-bed configuration should also facilitate removal of reaction heat and provide a steady selectivity to product composition. However, the fluidized-bed reactor for this particular application may be a very costly item to design and construct as it may have to deal with a high density gas due to the large amount of higher molecular weight Br contained in the reactor feed (in the forms of HBr and alkyl bromides). Elevated operating pressure, 20-50 bars, may be required to minimize the recompression cost of recycle methane, which, however, will further increase the density of the gases in the synthesis reactor, resulting in a large diameter reactor with heavy wall thickness.

In product recovery, fresh feed gas may be required to replace the lower molecular weight alkanes converted to products. The fresh feed gas stream containing, for example, primarily methane may necessitate sufficient treating to remove excessive amounts of ethane and higher hydrocarbons prior to being combined with bromine and reacted in a bromination reactor. The feed gas stream may or may not mix with the hydrocarbon mixture exiting HBr recovery prior to receiving such treating. While some ethane and higher hydrocarbons may be tolerated in the bromination reactor, due to the much higher bromination rate of the higher hydrocarbons than that of methane, higher concentrations of the higher hydrocarbon impurities may easily over-brominate and, thus, may result in the rapid formation of carbon-containing coke-like solids, which can cause yield loss and reduced process reliability by fouling and plugging the reactor as well as the downstream units. However, the removal of ethane and higher hydrocarbons from the methane by such means as adsorption or cryogenic distillation can be costly. The cost is higher when both the recycle methane and the fresh feed gas stream require the removal of ethane and higher hydrocarbons. The cost is even higher when high methane-to-bromine ratios are used in the bromination, leading to a large flow rate of recycle methane.

Thus, although progress has been made in the conversion of lower molecular weight alkanes to higher molecular weight hydrocarbons, there remains a need for processes that are more efficient, economic, and safe to operate.

SUMMARY

To achieve the foregoing and other objects, and in accordance with the purposes of the present invention, as embodied and broadly described herein, one embodiment of the present invention is a process comprising reacting at least gaseous alkanes and a halogen (e.g., bromine) to produce at least a halogenation product stream, wherein the halogenation product stream comprise alkyl halides, hydrogen halide, and unreacted alkanes. Embodiments of the process further may comprise separating the halogenation product stream into at least a gaseous stream and a liquid alkyl halides stream, wherein the gaseous stream comprises hydrogen halide and unreacted alkanes, and wherein the liquid alkyl halides stream comprises alkyl halides. Embodiments of the process further may comprise recovering at least a portion of the hydrogen halide from the gaseous stream. Embodiments of the process further may comprise reacting at least a portion of the alkyl halides from the liquid alkyl halides stream in the presence of a catalyst to produce a synthesis product stream, wherein the synthesis product stream comprises higher molecular weight hydrocarbons and hydrogen halides.

Another embodiment of the present invention provides a process comprising reacting at least gaseous alkanes and bromine in a bromination reactor to produce at least a bromination product stream, wherein the bromination product stream comprise alkyl bromides, HBr, and unreacted alkanes. Embodiments of the process further may comprise separating the bromination product stream into at least a gaseous alkane/HBr stream and a liquid alkyl bromides stream, wherein the gaseous alkane/HBr stream comprises HBr and unreacted alkanes, and wherein the liquid alkyl bromides stream comprises alkyl bromides. Embodiments of the process further may comprise reacting at least a portion of the alkyl bromides from the liquid alkyl bromides stream in a synthesis reactor to produce a synthesis product stream, wherein the synthesis product stream comprises higher molecular weight hydrocarbons and HBr. Embodiments of the process further may comprise recovering at least a portion of the HBr from the synthesis product stream in an HBr separator. Embodiments of the process further may comprise providing a natural gas stream. Embodiments of the process further may comprise separating at least the synthesis product stream and the natural gas stream into at least a light ends product stream, a heavy ends product stream, and a feed gas stream, wherein the light ends product stream comprises hydrocarbons having from 2 to 4 carbons, wherein the heavy ends product stream comprises hydrocarbons having 5 or more carbons, and wherein the feed gas stream comprises methane. Embodiments of the process further may comprise compressing the feed gas stream in a feed compressor. Embodiments of the process further may comprise feeding the feed gas stream into the bromination reactor. Embodiments of the process further may comprise generating a recycle alkane stream by recovering at least a portion of the HBr from the gaseous alkane/HBr stream in a second hydrogen bromide separator operating at a higher pressure than the hydrogen bromide separator. Embodiments of the process further may comprise compressing the recycle alkane stream in a recycle compressor. Embodiments of the process further may comprise feeding the recycle alkane stream to the bromination reactor.

Another embodiment of the present invention is a system comprising a bromination reactor for reacting at least gaseous alkanes and bromine to produce at least a bromination product stream, wherein the bromination product stream comprises alkyl bromides, HBr, and unreacted alkanes. Embodiments of the system further may comprise an alkyl bromides fractionation unit in fluid communication with the bromination reactor for separating the bromination product stream into at least a gaseous alkane/HBr stream and a liquid stream, wherein the gaseous alkane/HBr stream comprises HBr and unreacted alkanes, and wherein the liquid stream comprises alkyl bromides. Embodiments of the system further may comprise a synthesis reactor in fluid communication with the alkyl bromides fractionation unit for reacting at least a portion of the alkyl bromides from the liquid stream in the presence of a catalyst to produce a synthesis product stream, wherein the synthesis product stream comprises higher molecular weight hydrocarbons and HBr. Embodiments of the system further may comprise an HBr separator in fluid communication with the synthesis reactor for recovering at least a portion of the HBr from the synthesis product stream. Embodiments of the system further may comprise a second HBr separator unit in fluid communication with the alkyl bromides fractionation unit for recovering at least a portion of the HBr from the gaseous alkane/HBr stream.

BRIEF DESCRIPTION OF THE DRAWINGS

These drawings illustrate certain aspects of some of the embodiments of the present invention and should not be used to limit or define the invention.

DETAILED DESCRIPTION OF SPECIFIC EMBODIMENTS

Figure 1:
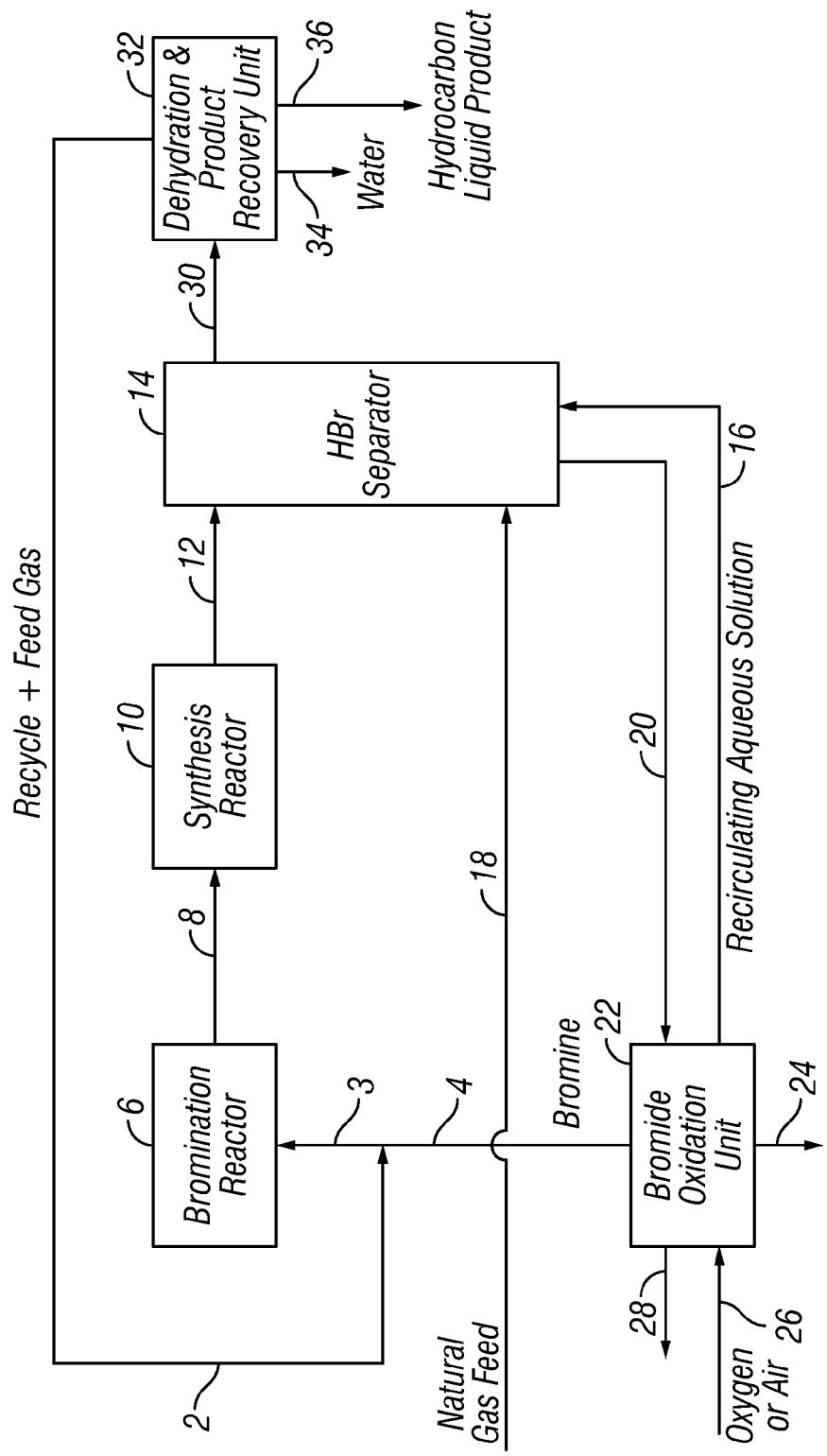
FIG. 1 is a schematic view of a prior art process for the conversion of lower molecular weight alkanes to higher molecular weight hydrocarbons.

Embodiments of the present invention are directed to processes for converting lower molecular weight alkanes to higher molecular weight hydrocarbons that include demethanization of brominated hydrocarbons, wherein the brominated hydrocarbons are formed by reaction of the lower molecular weight alkanes with bromine.

There may be many potential advantages to the methods and systems of the present invention, only some of which are alluded to herein. One of the many potential advantages of the systems and methods of the present invention is that separation of the methane from the brominated hydrocarbons should reduce the large recycle stream circulating through the entire process due to the large excess methane that may be used in the bromination step. Accordingly, the bromination step can be performed with a large methane-to-bromine ratio with reasonable recompression cost for recycled methane as embodiments. In addition, reduction of the large recycle stream circulating throughout the entire system should also reduce the cost for ethane separation as the recycle stream should not need to be treated for ethane removal while still meeting the ethane specification for feed to the bromination step. Yet another potential advantage of the systems and methods of the present invention is that separation of the methane from the brominated hydrocarbons should reduce the feed rate to the synthesis reactor in the alkyl bromide conversation step. Accordingly, the size of the synthesis reactor can be reduced, which may result in considerable costs savings, especially if a fluidized bed reactor is employed.

The term "higher molecular weight hydrocarbons" as used herein refers to hydrocarbons comprising a greater number of carbon atoms than one or more components of the feedstock. For example, natural gas is typically a mixture of light hydrocarbons, predominately methane, with lesser amounts of ethane, propane, and butane, and even smaller amounts of longer chain hydrocarbons such as pentane, hexane, etc. When natural is used as a feedstock, higher molecular weight hydrocarbons produced in accordance with embodiments of the present invention may include a hydrocarbon comprising C2 and longer hydrocarbon chains, such as propane, butane, C5+ hydrocarbons, aromatic hydrocarbons, and mixtures thereof. In some embodiments, part or all of the higher molecular weight hydrocarbons may be used directly as a product (e.g., LPG, motor fuel, etc.). In other instances, part or all of the higher molecular weight hydrocarbons may be used as an intermediate product or as a feedstock for further processing. In yet other instances, part or all of the higher molecular weight hydrocarbons may be further processed, for example, to produce gasoline grade fuels, diesel grade fuels, and fuel additives. In some embodiments, part or all of the higher molecular weight hydrocarbons obtained by the processes of the present invention can be used directly as a motor gasoline fuel having a substantial aromatic content, as a fuel blending stock, or as feedstock for further processing such as an aromatic feed to a process producing aromatic polymers such as polystyrene or related polymers.

The end use of the higher molecular weight hydrocarbons may depend on the particular catalyst employed in the oligomerization portion of the methods discussed below, as well as the operating parameters employed in the process. Other uses will be evident to those skilled in the art with the benefit of this disclosure.

The term "alkyl bromides," as used herein, refers to mono-, di-, and tri-brominated alkanes, and combinations of these. Poly-brominated alkanes include di-brominated alkanes, tri-brominated alkanes and mixtures thereof. These alkyl bromides may then be reacted over suitable catalysts so as to form higher molecular weight hydrocarbons.

Lower molecular weight alkanes may be used as a feedstock for the methods described herein. A suitable source of lower molecular weight alkanes may be natural gas. As used herein, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or clathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

Suitable sources of bromine that may be used in various embodiments of the present invention include, but are not limited to, elemental bromine, bromine salts, aqueous hydrobromic acid, metal bromide salts, and the like. Combinations may be suitable, but as recognized by those skilled in the art, using multiple sources may present additional complications.

FIG. 1 is a schematic diagram illustrating a prior art process for the conversion of gaseous alkanes to higher molecular weight hydrocarbons via a bromine-based method. An example of a bromine-based method for the conversion of gaseous alkanes to higher molecular weight hydrocarbons is described in more detail in U.S. Pat. No. 7,674,941, the disclosure of which is incorporated herein by reference.

As illustrated, a gas stream 2 comprising lower molecular weight alkanes (which, in some embodiments, may include a mixture of a feed gas plus a recycled gas stream) and a bromine stream 4 may be combined and introduced into a bromination reactor 6. In the illustrated embodiment, the gas stream 2 and the bromine stream 4 are premixed to form a bromination feed gas stream 3 prior to feeding the bromination reactor 6. In an alternative embodiment (not illustrated), the gas stream 2 and bromine stream 4 may be combined in the bromination reactor 6. The gas stream 2 and the bromine stream 4 may be allowed to react in the bromination reactor 6 to form a bromination product stream 8 that comprise alkyl bromides, HBr vapor, and unreacted alkanes. The bromination product stream 8 may be withdrawn from the bromination reactor 6.

The bromination product stream 8 from the bromination reactor 6 may be fed to the synthesis reactor 10. In the synthesis reactor 10, the alkyl bromides in bromination product stream 8 are then reacted over a suitable catalyst under sufficient conditions via a catalytic coupling reaction to produce higher molecular weight hydrocarbons and additional HBr vapor. Those of ordinary skill in the art will appreciate, with the benefit of this disclosure, that the particular hydrocarbons products produced will be dependent, for example, upon the catalyst employed, the composition of the alkyl bromides introduced, and the exact operating parameters employed. Catalysts that may be employed in the synthesis reactor 10 include synthetic crystalline alumino-silicate catalyst as will be recognized by those of ordinary skill in the art. A synthesis product stream 12 comprising the higher molecular weight hydrocarbons and additional HBr vapor may be withdrawn from the synthesis reactor 10. As discussed below, this methane produced in the synthesis reactor 10 may be separated from the higher molecular weight hydrocarbons and recycled to the bromination reactor 6. In some embodiments, the synthesis product stream 12 further may comprise an unintended amount of methane produced in the synthesis reactor 10, unreacted alkanes (e.g., methane) in the reactor feed, and the HBr vapor produced in the synthesis reactor 10.

The synthesis product stream 12 from the synthesis reactor 10 may then be contacted with an aqueous solution in an HBr separator 14 to recover HBr from the hydrocarbons by absorbing it into the aqueous solution. The aqueous solution may be fed to the HBr separator via recirculating aqueous solution 16. The resultant aqueous solution comprising HBr dissolved therein may also be contacted with a feed gas stream 18 (e.g., natural gas) comprising lower molecular weight alkanes to strip out any residual hydrocarbons, depending on the solubility of the hydrocarbons in the aqueous solution at the operating conditions. The resultant aqueous solution comprising HBr dissolved therein may be removed from the HBr separator 14 via aqueous HBr stream 20.

The aqueous HBr stream 20 may then be routed to a bromide oxidation unit 22 to convert the dissolved HBr to elemental bromine using, for example, air or oxygen and to regenerate the aqueous solution for reuse in the HBr separator 14. The regenerated aqueous solution may then be recirculated to the HBr separator via recirculating aqueous solution 16. The bromine may then be treated sufficiently and sent to the bromination reactor 6 via bromine stream 4. In some embodiments, the bromine that is feed into the bromination reactor 6 may be dry bromine in that the bromine is substantially water-free. Effluent water 24 may also be removed from this oxidation unit 22. Line 26 may be used to supply the oxygen or air fed to this oxidation unit. Residual oxygen or spent air may be removed from the oxidation unit via line 28.

The hydrocarbon stream 30 comprising the unreacted alkanes, product hydrocarbons, and the feed gas may be withdrawn from the HBr separator 14. The hydrocarbon stream 30 may substantially HBr free, in accordance with embodiments of the present invention, for example, containing less than about 1 mppm HBr and alternatively less than 0.1 mppm HBr. As illustrated, the hydrocarbon stream 30 may be routed to a dehydration and product recovery unit 32 wherein water is removed from the remaining constituents, higher molecular weight hydrocarbons may be recovered as liquid hydrocarbon products, and lower molecular weight alkanes may be recycled with feed gas to the bromination reactor 6. As illustrated, water may be removed via water stream 34. A liquid hydrocarbon product stream 36 comprising higher molecular weight hydrocarbons may be withdrawn for use as a fuel, a fuel blend, or for further petrochemical or fuel processing, for example. As illustrated, gas stream 2 comprising the feed gas and unreacted methane and potentially other unreacted alkanes may be recycled to the bromination reactor 6.

Figure 2:
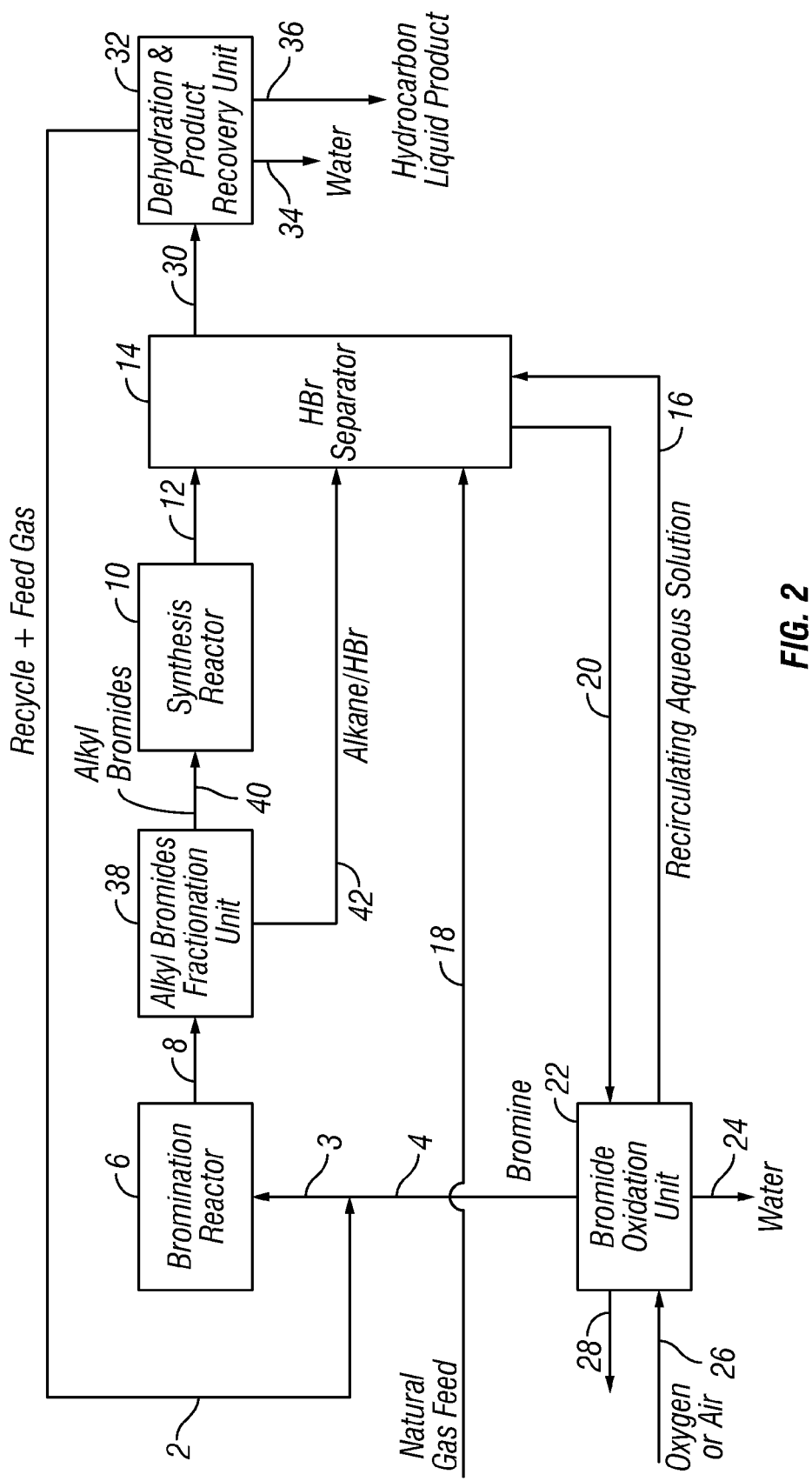
FIG. 2 is a schematic view of a process for the conversion of lower molecular weight alkanes to higher molecular weight hydrocarbons that includes demethanization of brominated hydrocarbons in accordance with one embodiment of the present invention.

Referring now to FIG. 2, a bromine-based process is illustrated for the conversion of lower molecular weight alkanes to higher molecular weight hydrocarbons that includes demethanization of brominated hydrocarbons in accordance with one embodiment of the present invention. The illustrated embodiment is similar to that illustrated by FIG. 1 except that there is an additional unit between the bromination reactor 6 and the synthesis reactor 10.

As illustrated, the bromination product stream 8 comprising alkyl bromides, HBr vapor, and unreacted alkanes can be withdrawn from the bromination reactor 6 and fed to an alkyl bromides fractionation unit 38. In the alkyl bromides fractionation unit 38, the bromination product stream 8 may be separated into a liquid alkyl bromides stream 40 comprising methyl bromide and other heavier alkyl bromides and a gaseous alkane/HBr stream 42 comprising unreacted alkanes and HBr.

In some embodiments, the liquid alkyl bromides stream 40 comprising methyl bromide and other heavier alkyl bromides may be vaporized and fed to the synthesis reactor 10. In the synthesis reactor 10, the alkyl bromides may be reacted over a suitable catalyst under sufficient conditions via a catalytic coupling reaction to produce higher molecular weight hydrocarbons and additional HBr vapor. The synthesis product stream 12 comprising the higher molecular weight hydrocarbons and additional HBr may be withdrawn from the synthesis reactor 10 and fed to the HBr separator 14 for recovery of HBr.

In some embodiments, the gaseous alkane/HBr stream 42 comprising the unreacted alkanes and HBr produced in the bromination reactor 6 may be also routed to the HBr separator 14 to recover HBr from the alkanes. While not illustrated, the gaseous alkane/HBr stream 42 and the synthesis product stream 12 may be mixed prior to contacting the recirculating aqueous solution 16 in the HBr separator 14. By routing the gaseous alkane/HBr stream 42 to the HBr separator 14, in some embodiments, the unreacted alkanes and HBr separated from the alkyl bromides in the alkyl bromides fractionation unit 38 are not fed to the synthesis reactor 10. Accordingly, in accordance with embodiments, the feed to the synthesis reactor 10 is reduced, and the size of the synthesis reactor 10 can be reduced, resulting in cost savings, especially if a fluidized bed reactor is employed.

Figure 3:
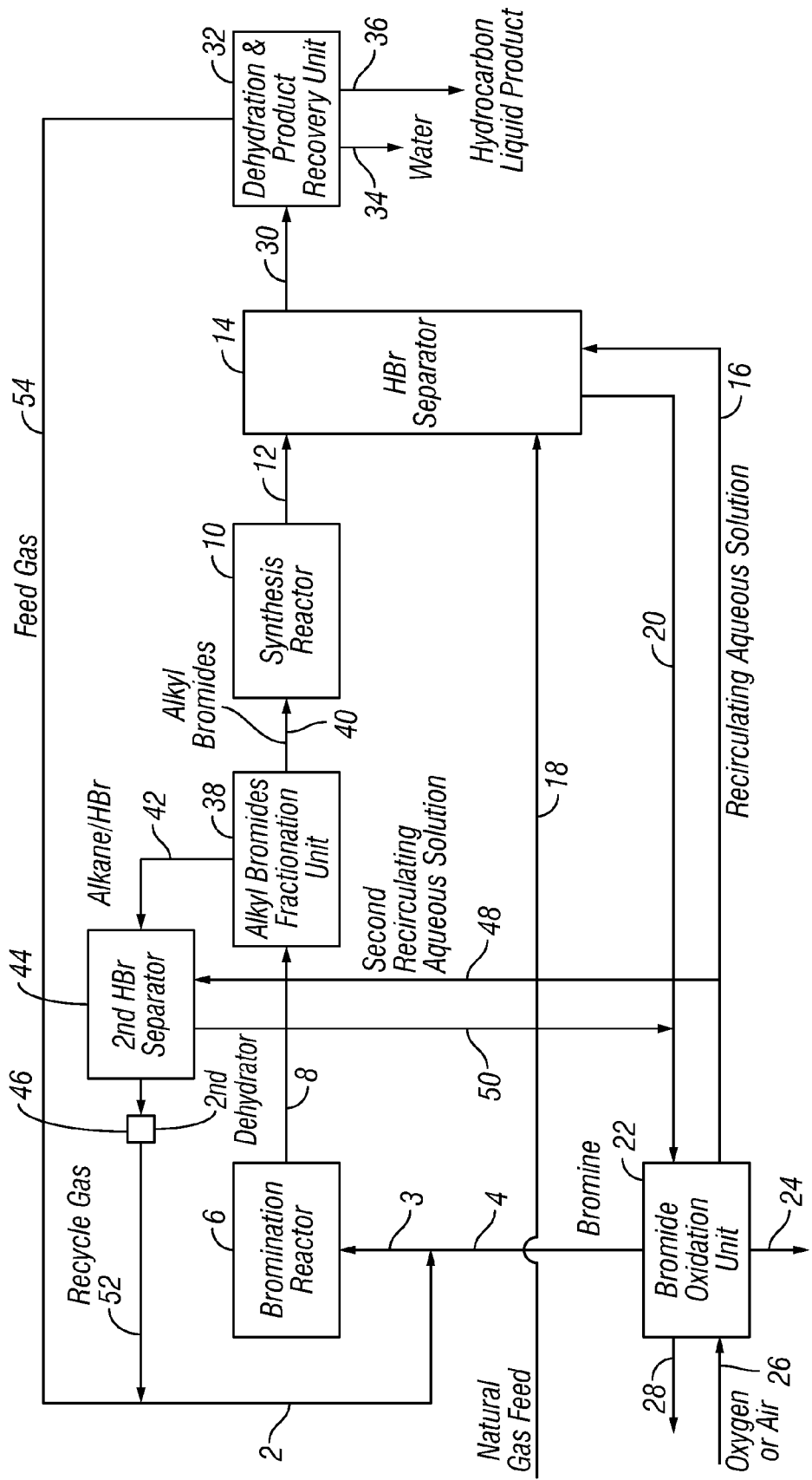
FIG. 3 is a schematic view of another embodiment of a process of the present invention for the conversion of lower molecular weight alkanes to higher molecular weight hydrocarbons that includes demethanization of brominated hydrocarbons.

Referring now to FIG. 3, a bromine-based process is illustrated for the conversion of lower molecular weight alkanes to higher molecular weight hydrocarbons that includes demethanization of brominated hydrocarbons in accordance with another embodiment of the present invention. The illustrated embodiment is similar to that illustrated by FIG. 2 except that the gaseous alkane/HBr stream 42 comprising the alkanes and HBr separated from the alkyl bromides in the alkyl bromides fractionation unit 38 bypasses the dehydration and product recovery unit 32 by using a second HBr separator 44 with recycle of the alkanes via stream 52 to the bromination reactor 6 after a second dehydrator 46. Because the recycle gas stream 52 does not contain higher molecular weight hydrocarbons but low molecular weight hydrocarbons, it can be recycled to the bromination reactor 6 for reuse, in accordance with embodiments of the present invention. In some embodiments, the recycle gas stream 52 comprises HBr and methane and is essentially free of C2+ alkanes. For example, the recycle gas stream 52 may comprise C2+ alkanes in an amount of less than about 1 mole %.

As illustrated, the gaseous alkane/HBr stream 42 comprising the unreacted alkanes and HBr may be withdrawn from the alkyl bromides fractionation unit 38 and fed to a second HBr separator 44. In the second HBr separator 44, any of a variety of different suitable techniques may be used to produce a recycle gas stream 52 by separation of HBr, including, but not limited to, the techniques disclosed in U.S. Pat. No. 7,674,941, the disclosure of which is incorporated herein by reference. Non-limiting examples of techniques for HBr separation include absorption HBr into an aqueous solution or adsorption of HBr on a metal oxide. In some embodiments, the HBr can be recovered from the unreacted alkanes by adsorbing the HBr into an aqueous solution using, for example, a packed column or other suitable containing device. The aqueous solution may be fed to the second HBr separator via second recirculating aqueous stream 48.

The second HBr separator 44 can operate at a different, and preferably, higher pressure than the HBr separator 14 which recovers HBr from the synthesis product stream 12. For example, the second HBr separator 44 can operate at a pressure that is at least about 3 bars higher than the HBr separator 14. In some embodiments, the second HBr separator 44 may operate at a pressure of about 5 bars to about 50 bars while the HBr separator 14 operates at a pressure a pressure of about 2 bars to about 47 bars.

The resultant aqueous solution comprising HBr dissolved therein may be removed from the second HBr separator 44 via second aqueous HBr stream 50, in accordance with embodiments of the present invention. The second aqueous HBr stream 50 may be combined with aqueous HBr stream 20 from the HBr separator 14 and fed to the bromide oxidation unit 22 described above to produce elemental bromine and regenerate the aqueous solutions for reuse in the HBr separator 14 and the second HBr separator 44. While FIG. 3 illustrates combination of the aqueous HBr stream 20 and the second aqueous HBr stream 50 prior to entering the bromide oxidation unit 22, embodiments (not illustrated) may include separately feeding the aqueous HBr streams 20, 50 to the bromide oxidation unit 22.

The recycle gas stream 52 containing the alkanes separated from HBr in the second HBr separator 44 may be fed to a second dehydrator 46 for the removal of water and then mixed with a feed gas stream 54 from the dehydration and product recovery unit 32. The gas stream 2 comprising a mixture of the recycle gas stream 52 and the feed gas stream 54 may be fed to the bromination reactor 6. While FIG. 3 illustrates combination of the recycle gas stream 52 and the feed gas stream 54 prior to entering the bromination reactor 6, embodiments (not illustrated) may include separately feeding the recycle gas stream 52 and the feed gas stream 54 to the bromination reactor 6.

In the illustrated embodiment, the unreacted alkanes separated from the alkyl bromides in the alkyl bromides fractionation unit 38 are only circulating through the bromination reactor 6, the alkyl bromides fractionation unit 38, the second HBr separator 44, and the second dehydrator 46, enduring much less pressure drop by avoiding circulation through the entire system as disclosed in the process schemes used heretofore. As a result, the increase in compression cost for using a large excess of methane or high methane-to-bromine ratio in the bromination reactor 6 can be minimized by incorporation of embodiments of the present invention.

Figure 4A:
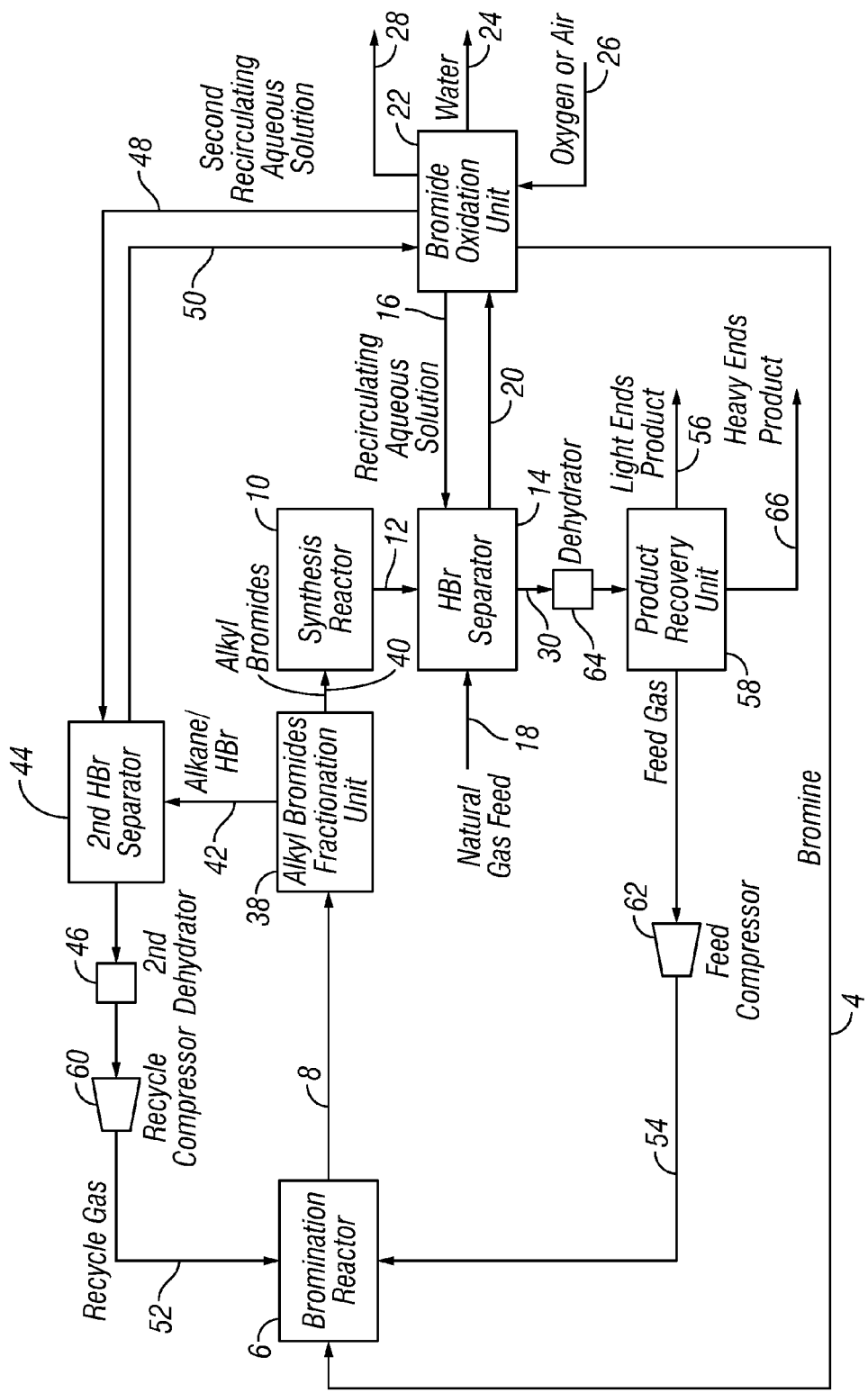
FIG. 4A is a schematic view of another embodiment of a process of the present invention for the conversion of lower molecular weight alkanes to higher molecular weight hydrocarbons that includes demethanization of brominated hydrocarbons, which also produces light end hydrocarbons as another product.

Referring now to FIG. 4A, a bromine-based process is illustrated for the conversion of lower molecular weight alkanes to higher molecular weight hydrocarbons that includes demethanization of brominated hydrocarbons in accordance with another embodiment of the present invention. The illustrated embodiment is similar to that illustrated in FIG. 3 except that a light ends product stream 56 comprising light end hydrocarbons (C2-C4) is specified as an additional product from the product recovery unit 58. It should be understood that when the light end hydrocarbons are recovered in the light ends product stream 56 as an additional product, the feed gas stream 54 routed to the bromination reactor may contain substantially pure methane, in some embodiments, in that the C2+ alkane concentration in the feed gas stream 54 may be less than 1 mole %, in one embodiment, and less than about 0.1 mole %, in another embodiment.

As illustrated, the bromination reactor 6 may receive as feed the recycle gas stream 52 from the recycle compressor 60, the feed gas stream 54 from the feed compressor 62, and the bromine stream 4 from the bromide oxidation unit 22. While not illustrated, embodiments may include pre-mixing two or more of these feed streams prior to feeding the bromination reactor 6. The recycle gas stream 52 and the feed gas stream 54 may be allowed to react with the bromine stream 4 to form a bromination product stream 8 that comprise alkyl bromides, HBr vapor, and unreacted alkanes. The bromination product stream 8 may be withdrawn from the bromination reactor 6.

In the bromination reactor 6, the lower molecular weight alkanes in the feed gas stream 54 and the recycle gas stream 52 may be reacted exothermically with bromine in the bromine stream 4, for example, at a temperature in the range of about 250° C. to about 600° C., and at a pressure in the range of about 1 bar to about 50 bars to produce gaseous alkyl bromides and HBr. In an embodiment, the operating pressure of the bromination reactor 6 may range from about 20 bars to about 40 bars, for example, to minimize recompression costs and to maximize the condenser temperature required for the alkyl bromides fraction step. In some embodiments, the feeds to the bromination reactor 6 may be pre-heated to a temperature of about 250° C. to about 400° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art will appreciate that the bromination reaction may be a non-catalytic (thermal) or a catalytic reaction as described, for example, in U.S. Pat. No. 7,674,941. In the case of methane, it is believed that the formation of multiple brominated compounds occurs in accordance with the following general overall reaction:

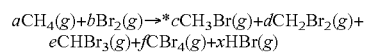

The methane/bromine molar ratio of the feed introduced to the bromination reactor 6 may be at least about 2.5:1, in some embodiments. In alternative embodiments, a larger excess of methane (e.g., about 3:1 to about 10:1) may be used in order to achieve desirable selectivity of methyl bromide and reduce the formation of soot, as methyl bromide is more rapidly brominated than methane under free radical conditions. The C2+ alkanes entering the bromination reactor 6 are known to more rapidly form poly-brominated alkanes and coke/soot, as they are much more easily brominated than methane. Accordingly, in some embodiments, the C2+ alkane content entering the bromination reactor 6 can be controlled by treating the natural gas feed stream 18 or its mixture with the higher molecular weight hydrocarbons formed in the synthesis reactor 10 using any suitable means, such as a cryogenic separation. In some embodiment, the C2+ alkane concentration in the total alkanes (recycle gas stream 52+feed gas stream 54) fed to the bromination reactor 6 is about 0.1 mole % to about 10 mole %, in another embodiment, about 0.1 mole % to about 1 mole %, and, in yet another embodiment, about 0.1 mole % to about 0.2 mole %.

As illustrated, the bromination product stream 8 comprising alkyl bromides, HBr vapor, and unreacted alkanes can be withdrawn from the bromination reactor 6 and fed to an alkyl bromides fractionation unit 38. In the alkyl bromides fractionation unit 38, the bromination product stream 8 may be separated into a liquid alkyl bromides stream 40 comprising methyl bromide and other heavier alkyl bromides and a gaseous alkane/HBr stream 42 comprising unreacted alkanes and HBr.

The gaseous alkane/HBr stream 42 comprising the unreacted alkanes and HBr may be withdrawn from the alkyl bromides fractionation unit 38 and fed to a second HBr separator 44. In the second HBr separator 44, a recycle gas stream 52 may be produced by separation of HBr from the unreacted alkanes. The recycle gas stream 52 from the separator 44 may be fed to the second dehydrator 46 for removal of water and then to a recycle compressor 60 for recompression. After dehydration and recompression, the recycle gas stream 52 may be routed to the bromination reactor 6 without further cryogenic treatment. Therefore, the process cost to control the presence of C2+ alkanes in the bromination reactor 6 is independent of the molar ratio of methane to bromine. In other words, the use of a large excess of methane should not increase the process cost associated with C2+ alkane control.

In addition, in the illustrated embodiment, the unreacted alkanes separated from the alkyl bromides in the alkyl bromides fractionation unit 38 are only circulating through the bromination reactor 6, the alkyl bromides fractionation unit 38, the second HBr separator 44, the second dehydrator 46, and the recycle compressor 60 enduring much less pressure drop by avoiding circulation through the entire system as disclosed in the process schemes used heretofore. Therefore, the increase in compression cost for using a large excess of methane or high methane-to-bromine ratio in the bromination reactor 6 can be minimized by incorporation of embodiments of the present invention.

In some embodiments, the liquid alkyl bromides stream 40 comprising methyl bromide and other heavier alkyl bromides may be vaporized and fed to the synthesis reactor 10. In one embodiment, the liquid alkyl bromides stream 40 can be pumped to a higher pressure before vaporization. In another embodiment, the liquid alkyl bromides stream 40 can be laid down to a lower pressure prior to vaporization. In the synthesis reactor 10, the alkyl bromides may be reacted over a suitable catalyst under sufficient conditions via a catalytic coupling reaction to produce higher molecular weight hydrocarbons and additional HBr vapor.

As illustrated, the synthesis product stream 12 comprising the higher molecular weight hydrocarbons and additional HBr may be withdrawn from the synthesis reactor 10 and fed to the HBr separator 14 for recovery of HBr. In the HBr separator 14 any of a variety of different suitable techniques may be used for separation of HBr, including, but not limited to, the techniques disclosed in U.S. Pat. No. 7,674,941, the disclosure of which is incorporated herein by reference. Non-limiting examples of techniques for HBr separation include absorption of HBr into an aqueous solution or adsorption of HBr on a metal oxide. The HBr separator 14 and the second HBr separator 44 may use the same or different techniques for the removal of HBr from the hydrocarbon streams (e.g., gaseous alkane/HBr stream 42, synthesis product stream 12). In some embodiments, the HBr separator 14 and the second HBr separator 44 operate at different pressures but both can interact with the bromide oxidation unit 22 for generation of elemental bromine and regeneration of the bromide-taking medium (e.g., aqueous solution, metal oxide adsorbent).

In the illustrated embodiment, the natural gas feed stream 18 comprising lower molecular weight alkanes may enter the HBr separator 14 for recovery of hydrocarbons or other purposes. While not illustrated by FIG. 4A, the natural gas feed stream 18 may alternatively be fed directly to the product recovery unit 58 for removal of C2+ hydrocarbons. While the present embodiment describes the use of natural gas feed stream 18, as discussed above, embodiments of the present invention encompass the use of other feedstocks of lower molecular weight alkanes.

The hydrocarbon stream 30 comprising the unreacted alkanes, higher molecular weight hydrocarbons, and the feed gas may be withdrawn from the HBr separator 14 and routed to a dehydrator 64 for removal of water and then a product recovery unit 58 for recovery of a heavy ends product stream 66 comprising heavy end hydrocarbons (C5+), a light ends product stream 56 comprising light end hydrocarbons (C2-C4), and a feed gas stream 54 comprising methane. Any suitable method of dehydration and product recovery may be used, including, but not limited to, solid-bed desiccant adsorption followed by refrigerated condensation, cryogenic separation, or circulating absorption oil or some other solvent.

The feed gas stream 54 from the product recovery unit 58 may be fed to the bromination reactor 6 via the feed compressor 62. It should be understood that the feed gas stream 54 may also comprise some C2+ alkanes so long as the C2+ content of the alkanes (feed gas stream 54+recycle gas stream 52) fed to the bromination reactor 6 is less than a predetermined value.

Figure 4B:
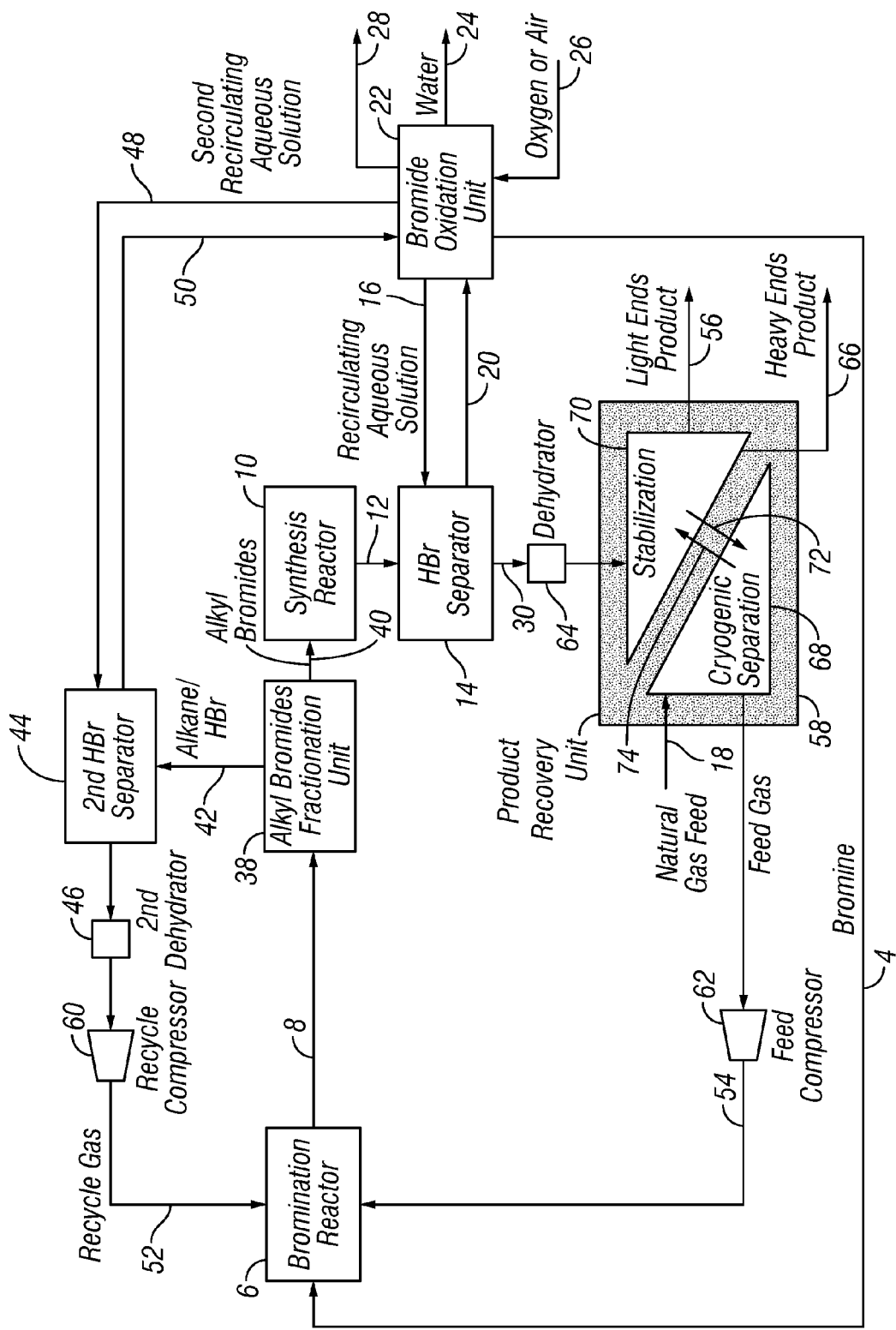
FIG. 4B is a schematic view of the embodiment illustrated in FIG. 4A depicting an alternative processing scheme which may be used in which natural gas is fed directly to the product recovery step in accordance with one embodiment of the present invention.

Referring now to FIG. 4B, a bromine-based process is illustrated for the conversion of lower molecular weight alkanes to higher molecular weight hydrocarbons that includes demethanization of brominated hydrocarbons in accordance with another embodiment of the present invention. The illustrated embodiment is similar to that illustrated in FIG. 4A except that the natural gas feed stream 18 directly feeds the product recovery unit 58.

The product recovery unit 58 illustrated in FIG. 4B generally comprises a cryogenic separation section 68 and a stabilization section 70. As illustrated, the stabilization section 70 may be fed by the hydrocarbon stream 30 exiting the HBr separator 14 after the dehydrator 64. In one embodiment, the stabilization section 70 produces C5+ hydrocarbons as a heavy ends product stream 66, C2-C4 light end hydrocarbons as a light ends product stream 56, and a minor stream 72 containing methane. As illustrated, the minor stream 72 may be routed to the cryogenic separation section 68, which may also be fed by the natural gas feed stream 18. In one embodiment, the cryogenic separation section 68 produces a feed gas stream 54 comprising methane in which the C2+ content is lower or equal to a predetermined value and a hydrocarbon stream 74 comprising C2+ hydrocarbons which can be returned to the stabilization section 70 for recovery. The feed gas stream 54 may then compressed by a feed compressor 62 and combined with the recycle gas stream 52 and bromine stream 4 entering the bromination reactor 6. In some embodiments, the content of C2+ alkanes in the feed gas stream 54 should be low enough such that the C2+ alkane concentration in the total alkanes (feed gas stream 54+recycle gas stream 52) fed to the bromination reactor 6 is about 0.1 mole % to about 10 mole %, in another embodiment, about 0.1 mole % to about 1 mole %, and, in yet another embodiment, about 0.1 mole % to about 0.2 mole %.

Figure 5:
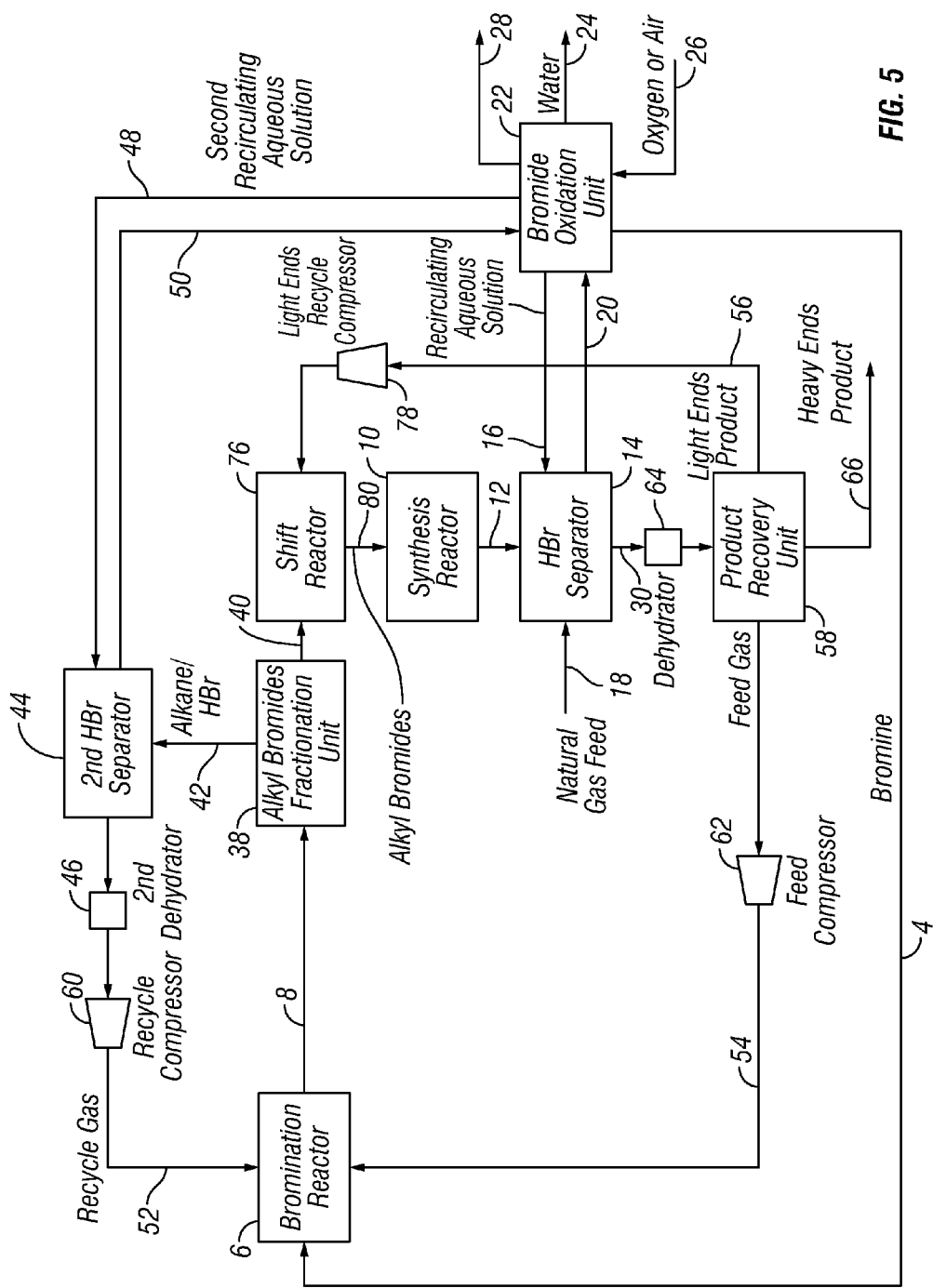
FIG. 5 is a schematic view of another embodiment of a process of the present invention for the conversion of lower molecular weight alkanes to higher molecular weight hydrocarbons that includes demethanization of brominated hydrocarbons configured to incorporate a shift reactor for reducing the content of poly-brominated alkanes fed to the synthesis reactor.

Referring now to FIG. 5, a bromine-based process is illustrated for the conversion of lower molecular weight alkanes to higher molecular weight hydrocarbons that includes demethanization of brominated hydrocarbons in accordance with another embodiment of the present invention. The illustrated embodiment is similar to that illustrated in FIG. 4A except that the light ends product stream 56 comprising light end hydrocarbons (C2-C4) is recycled to shift reactor 76 to reduce the content of poly-brominated alkanes in the feed to the synthesis reactor 10. It should be understood that when the light end hydrocarbons are recovered in the light ends product stream 56 as an additional product, the feed gas stream 54 routed to the bromination reactor may contain substantially pure methane, in some embodiments, in that the C2+ alkane concentration in the feed gas stream 54 may be less than 1 mole %, in one embodiment, and less than about 0.1 mole %, in another embodiment.

As illustrated, the light ends product stream 56 comprising light end hydrocarbons (C2-C4) may be fed to the shift reactor 76 via a light ends recycle compressor 78. The liquid alkyl bromides stream 40 from the alkyl bromides fractionation unit 38 comprising methyl bromide and other heavier alkyl bromides may also be fed to the shift reactor 76. In some embodiments, the feeds may be vaporized prior to their introduction into the shift reactor 76. In the shift reactor 76, at least a portion of the poly-brominated alkanes in the liquid alkyl bromides stream 40 can be reproportionated into mono-brominated alkanes, thus reducing the content of poly-brominated alkanes in the feed to the synthesis reactor 10. This shift reaction occurs by reaction of the C2-C4 hydrocarbons in the light ends product stream 56 with the poly-brominated alkanes to form mono-brominated alkanes, such as methyl bromide, ethyl bromide, propyl bromide, and the like. In some embodiments, the shift reaction may proceed thermally without a catalyst. In another embodiment, the shift reaction may be a catalytic reaction. Example techniques for reproportionation of poly-brominated alkanes via a shift reaction is described in more detail in U.S. Pat. No. 7,674,941, the disclosure of which is incorporated herein by reference. In the illustrated embodiment, synthesis reactor feed 80 comprising mono-brominated alkanes may be withdrawn from the shift reactor 76 and fed to the synthesis reactor 10.

Figure 6:
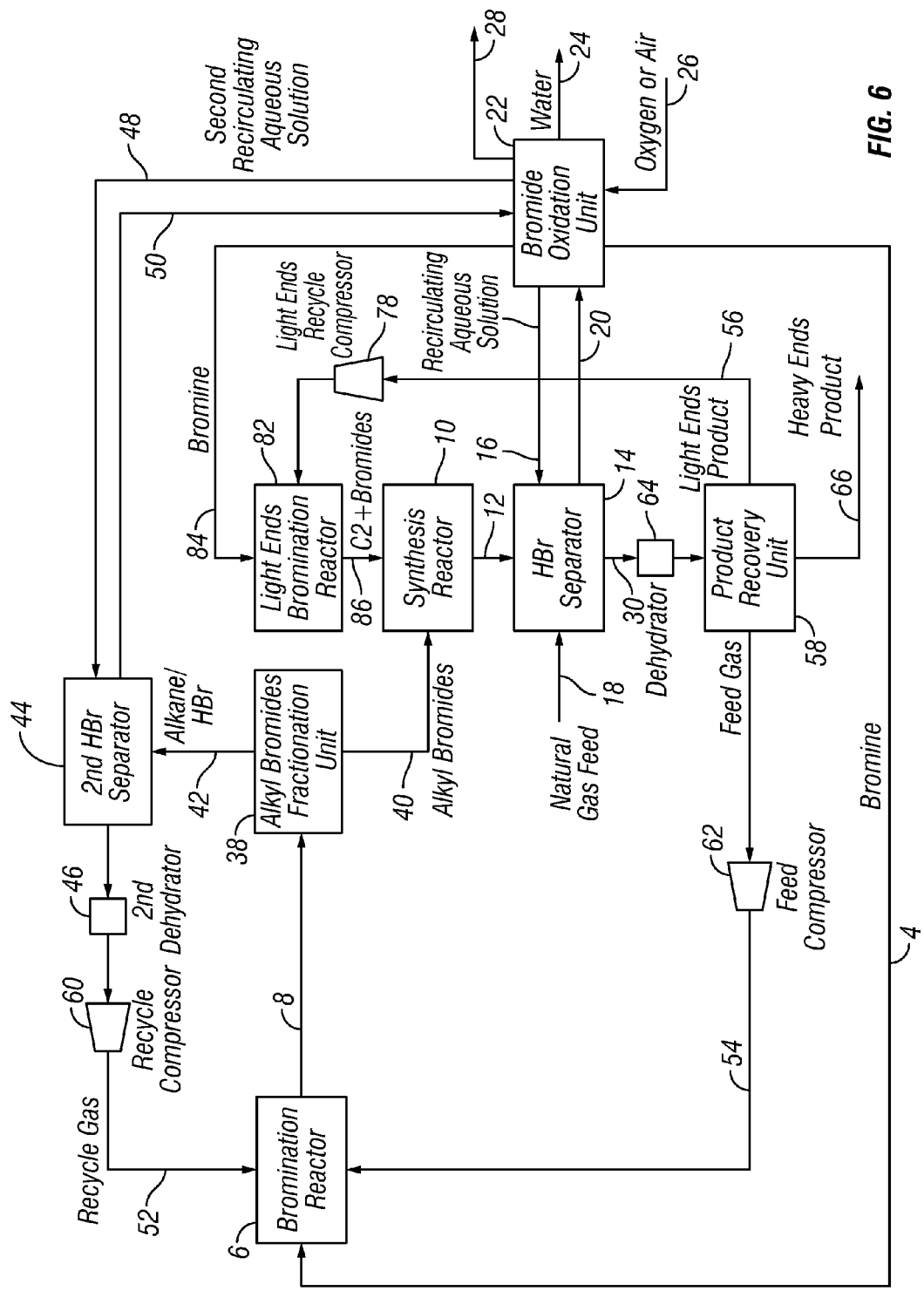
FIG. 6 is a schematic view of another embodiment of a process of the present invention for the conversion of lower molecular weight alkanes to higher molecular weight hydrocarbons that includes demethanization of brominated hydrocarbons with recycle of light end hydrocarbons to produce light end bromides for an additional feed to the synthesis reactor.

Referring now to FIG. 6, a bromine-based process is illustrated for the conversion of lower molecular weight alkanes to higher molecular weight hydrocarbons that includes demethanization of brominated hydrocarbons in accordance with another embodiment of the present invention. The illustrated embodiment is similar to that illustrated in FIG. 5 except that the light ends product stream 56 comprising light end hydrocarbons (C2-C4) is recycled to light ends bromination reactor 82 to produce C2+ bromides, preferably C2+ monobromides, for additional feed to the synthesis reactor 10. It should be understood that when the light end hydrocarbons are recovered in the light ends product stream 56 as an additional product, the feed gas stream 54 routed to the bromination reactor may contain substantially pure methane, in some embodiments, in that the C2+ alkane concentration in the feed gas stream 54 may be less than 1 mole %, in one embodiment, and less than about 0.1 mole %, in another embodiment.

As illustrated, the light ends product stream 56 may be fed to the light ends bromination reactor 82 via light ends recycle compressor 78. In the light ends bromination reactor 82, the light end hydrocarbons may be allowed to react with bromine fed to the reactor 82 via line 84 to form products that comprise C2+ alkyl bromides, HBr vapor, and unreacted light end hydrocarbons.

In some embodiments, the light ends bromination reactor 82 may operate at milder conditions than the bromination reactor 6. For example, the light ends bromination reactor 82 may operate at a temperature in the range of about 200° C. to about 500° C., alternatively about 235° C. to about 450° C., and alternatively about 250° C. to about 425° C. By way of further example, the light ends bromination reactor 82 may operate at a pressure in the range of about 1 bar to about 80 bars, alternatively about 10 bars to about 50 bars, and alternatively about 20 bars to about 40 bars. In one embodiment, the light ends bromination reactor 82 may operate at a temperature in the range of about 250° C. to about 425° C., and at a pressure in the range of about 15 bars to about 35 bars while the bromination reactor 6 may operate at a temperature in the range of about 350° C. to about 500° C. and a pressure of about 25 bars to about 40 bars.

The effluent that contains the C2+ alkyl bromides, HBr vapor, and unreacted light end hydrocarbons may be withdrawn from the light ends bromination reactor 82 and fed to the synthesis reactor 10 via line 86. While the effluent in line 86 from the light ends bromination reactor 82 and the liquid alkyl bromides stream 40 from the alkyl bromides fractionation 38 comprising methyl bromide and other heavier alkyl bromides are illustrated as separate feeds to the synthesis reactor 10, it should be understood that present embodiments encompass processes in which these streams are combined prior to the synthesis reactor 10.

Figure 7:
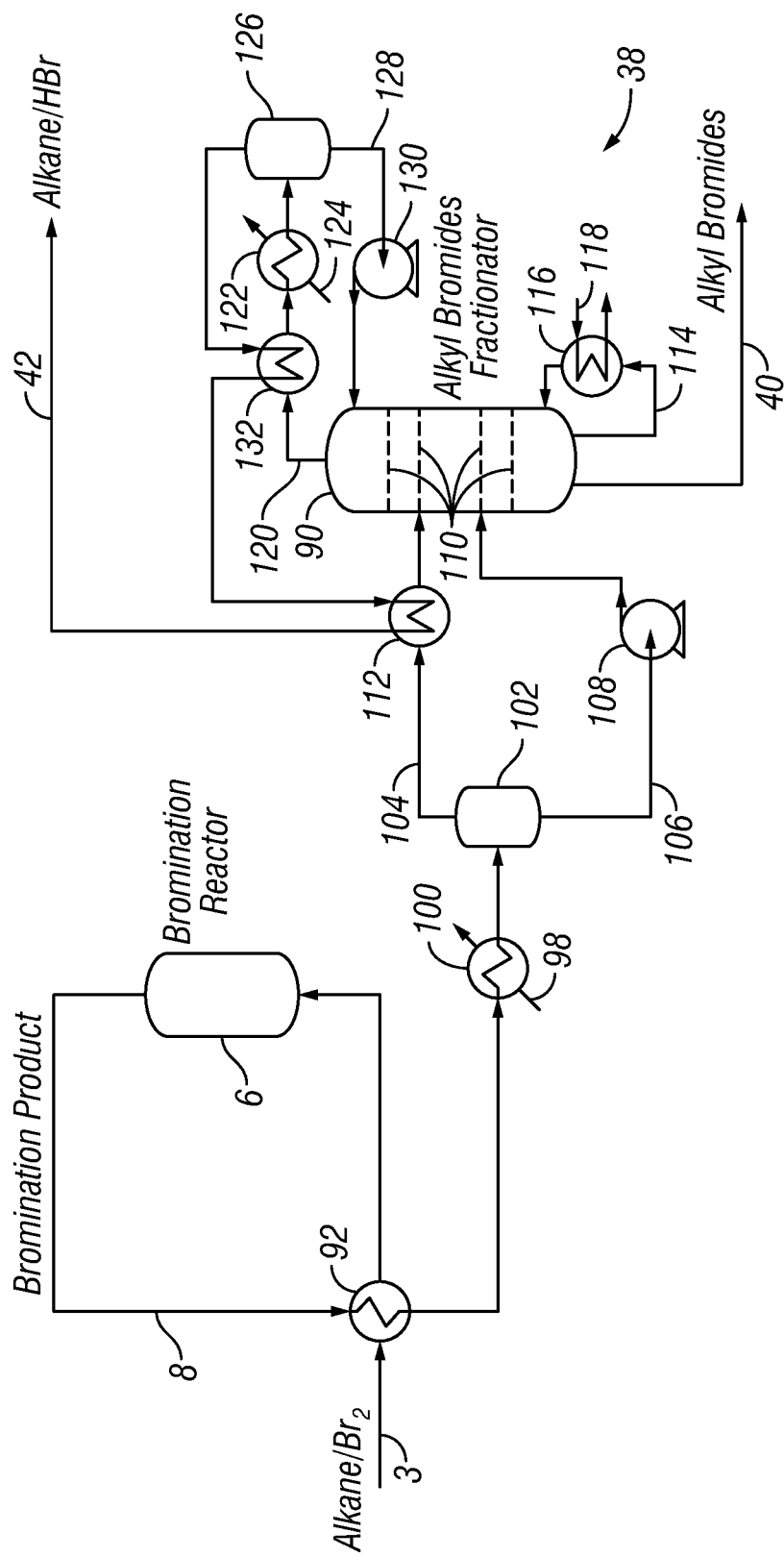
FIG. 7 is a schematic view of an alkyl bromides fractionation unit in accordance with one embodiment of the present invention.

Referring now to FIG. 7, an alkyl bromides fractionation unit 38 is illustrated for separating unreacted methane and HBr from methyl bromide and heavier bromides in the bromination product stream 8 leaving the bromination reactor 6 in accordance with one embodiment of the present invention.

As illustrated, a bromination feed gas stream 3 comprising lower molecular weight alkanes (which, in some embodiments, may include a mixture of a feed gas plus a recycled gas stream) and bromine may be introduced into a bromination reactor 6. In the bromination reactor 6, the lower molecular weight alkanes may be reacted exothermally with bromine at a relatively low temperature of about 250° C. to about 600° C. and at a pressure in the range of about 1 bar to about 50 bars to produce alkyl bromides and HBr vapor. To minimize recompression costs and to maximize condenser temperature in the alkyl bromides fractionator 90, the bromination reactor 6 may be operated, for example, at a pressure of about 20 bars to about 40 bars. A bromination product stream 8 comprising the alkyl bromides (e.g., $CH_3Br$ and other brominated methanes and ethanes), HBr vapor, and unreacted alkanes may be withdrawn from the bromination reactor 6.

In the illustrated embodiment, the bromination product stream 8 can first be cooled prior to entering the alkyl bromides fractionator 90 for separation of the unreacted methane and HBr from the alkyl bromides. As illustrated, the bromination product stream 8 may be first cooled by heating up the bromination feed gas stream 3 in a bromination feed/product cross heat exchanger 92. The bromination feed gas stream 3 may be heated in the bromination feed/product cross heat exchanger 92 to a temperature of about 250° C. to about 450° C., in one embodiment, and about 300° C. to about 400° C. in another embodiment. While not illustrated, the bromination product stream 8 may be further cooled, in some embodiments, by exchanging heat with one or more other process streams in one or more inlet cross heat exchangers. In one embodiment, the bromination product stream 8 may then be cooled, for example, to a temperature of about 33° C. to about 43° C., by exchanging heat with water stream 98 in water-cooled heat exchanger 100. It should be understood that a cooling medium other than water stream 98 may be used in some embodiments, for example, to obtain a lower temperature (e.g., about −10° C. to about 33° C.) for the bromination product stream 8 exiting the heat exchanger 100. The cooled bromination product stream 8, which partially condenses in the water-cooled heat exchanger 100, is then sent to an inlet separator 102 (e.g., drum) for vapor-liquid phase separation. As illustrated, the bromination product stream 8 may be separated into a gas stream 104 and a liquid stream 106 in the inlet separator 102. The liquid stream 106 may be introduced into a lower section of the alkyl bromides fractionator 90 via pump 108. The alkyl bromides fractionator 90 may include a liquid distributor or manifold (not shown) to more evenly distribute the liquid stream 106 throughout the internal cross sectional area of the alkyl bromides fractionator 90. The alkyl bromides fractionator 90 may comprise a number of trays or equivalent packing material, identified in FIG. 7 by reference number 110. The gas stream 104 from the inlet separator 102 may be further cooled, for example, to a temperature of about 10° C. to about 30° C., by exchanging heat in feed/overheads cross heat exchanger 112 with the gaseous alkane/HBr stream 42 from the overhead of the alkyl bromides fractionator 90 before being introduced into a higher section of the alkyl bromides fractionator 90.

In accordance with present embodiments, the alkyl bromides fractionator 90 should separate methyl bromide and heavier bromides from the effluent gas as a bottoms liquid product. The alkyl bromides fractionator 90 may operate at a pressure of about 1 bar to about 50 bars, alternatively about 20 bars to about 40 bars, and alternatively about 30 bars to about 35 bars. As illustrated, the bottoms liquid product can be withdrawn from at or near the bottom of the alkyl bromides fractionator 90 via liquid alkyl bromides stream 40. Liquid alkyl bromides stream 40 should generally comprise methyl bromide and other heavier bromides. In some embodiments, the liquid alkyl bromides stream 40 may comprise less than about 2% by weight of the total HBr introduced into the alkyl bromides fractionator 90, alternatively less than about 1%, and alternatively less than about 0.1%. Another stream 114 comprising methyl bromide and other heavier bromides be withdrawn from at or near the bottom of the alkyl bromides fractionator 90 and vaporized in reboiler 116, for example, by means of low pressure steam 118, in a manner that will be evident to those of ordinary skill in the art before being introduced back into the alkyl bromides fractionator 90 at or near the bottom thereof. In some embodiments, the reboiler 116 may operate to heat stream 114 to a temperature of about 100° C. to about 200° C.

The overhead vapor stream 120 may be withdrawn at or near the top of the alkyl bromides fractionator 90 and partially condensed in reflux condenser 122 against a refrigerant 124 and conveyed to a reflux separator drum 126. The reflux condenser 122 may operate to cool the overhead vapor stream 120 to a temperature of about −40° C. to about 0° C. In some embodiments, the overhead vapor stream 120 is cooled to a temperature greater than about −40° C. and greater than −34° C., in another embodiment. The reflux condenser 122 may have an operating pressure, for example, of about 20 bars to about 40 bars. The refrigerant 124 in the reflux condenser 122 may include propane or other available refrigerants. In the reflux separator drum 126, the overhead vapor stream 120 that was partially condensed in the reflux condenser 122 can be separated into a reflux stream 128 and a gaseous alkane/HBr stream 42. The reflux stream 128 may be conveyed via reflux pump 130 back into the alkyl bromides fractionator 90 at or near the top thereof. As illustrated, the gaseous alkane/HBr stream 42 exiting the reflux separator drum 126 may cross exchange in an overheads cross heat exchanger 132 with the overhead vapor stream 120 entering the reflux condenser 122 and in a feed/overheads cross heat exchanger 112 with the gas stream 104 entering the alkyl bromides fractionator 90, for example, to reduce refrigerant use. The gaseous alkane/HBr stream 42 from the reflux separator drum 126 may comprise, for example, HBr and unreacted alkanes (e.g., primarily methane with some heavier alkanes, such as ethane). In some embodiments, the gaseous alkane/HBr stream 42 comprises less than about 100 mppm alkyl bromides, alternatively less than about 10 mppm alkyl bromides, and alternatively less than about 1 mppm alkyl bromides.

As previously described, in accordance with embodiments of the present invention, the liquid alkyl bromides stream 40 can be vaporized and then conveyed to the synthesis reactor 10 (e.g., FIGS. 2-4, 6) for the production of higher molecular weight hydrocarbons or, in some embodiments, conveyed to a shift reactor 76 (e.g., FIG. 5) to reduce the content of poly-brominated alkanes in the feed to the synthesis reactor 10. In accordance with present embodiments, the gaseous alkane/HBr stream may be routed to other process units (e.g., HBr separator 14 illustrated on FIG. 2, second HBr separator 44 illustrated on FIG. 3) without entering the synthesis reactor 10.

While the preceding description is directed to bromine-based processes for the conversion of lower molecular weight alkanes to higher molecular weight hydrocarbons, it should be understood that chlorine or another suitable halogen may be used in accordance with present embodiments. Additionally, it should be understood that the present invention also encompasses conversion of lower molecular weight alkanes to other higher molecular weight hydrocarbons. For example, a catalyst may be selected in the synthesis reactor 10 (e.g., FIG. 2) for the production of olefins from alkyl bromides in a manner that will be evident to those of ordinary skill in the art.

To facilitate a better understanding of the present invention, the following examples of certain aspects of some embodiments are given. The following examples should not be read or construed in any manner to limit, or define, the entire scope of the invention.

Example 1

Simulations were conducted using Aspen Hysys V7.1 to analyze the inclusion of an alkyl bromides fractionation unit in a process for converting natural gas to liquid hydrocarbons via a bromine-based method. 50 MMSCFD of natural gas was fed to the process. A $Cl/Br_2$ mixture having a $Cl/Br_2$ molar ratio of 2.5 entered a bromination reactor at 150° to 300° C. and 35 Barg and left at 450° C. to 500° C. The conversion of $Br_2$ was 100%. The bromination product selectivity profile was: 70 mol % $CH_3Br$, 25 mol % $CH_2Br_2$, and 5 mol % other bromides and solid carbonaceous compounds. The bromination product stream rate was 11,822 kgmol/h. In the absence of an alkyl bromides fractionation unit, as illustrated in FIG.

1, the entire bromination product stream would be fed to a synthesis reactor. However, separating out the Cl/HBr from alkyl bromides by fractionation downstream of the bromination reactor, as illustrated in FIGS. 2-6, reduced the feed rate to the synthesis reactor by 78.6% to 2,528 kgmol/h. Essentially pure alkyl bromides may be fed to the synthesis reactor in the latter case with the alkyl bromides fractionation unit. Solid carbonaceous compounds may be filtered out prior to fractionation.

For comparison, a $Cl/Br_2$ molar ratio of 5 was used in the bromination reactor. The conversion of $Br_2$ was 100%. The bromination product selectivity profile was: 80 mol % $CH_3Br$, 15 mol % $CH_2Br_2$, and 5 mol % other bromides and solid carbonaceous compounds. In the absence of alkyl bromides fractionation unit, the entire bromination product stream (18,673 kgmol/h) fed the synthesis reactor. Separating out Cl/HBr from alkyl bromides by fractionation downstream of the bromination reactor, as illustrated in FIGS. 2-6, reduced the feed rate to the synthesis reactor by 86.5% to 2,526 kgmol/h. Essentially pure alkyl bromides may be fed to the synthesis reactor in the latter case with the alkyl bromides fractionation. Solid carbonaceous compounds may be filtered out prior to fractionation.

The above results are summarized in Table 1. Table 1 also shows that higher $CH_3Br$ selectivity was achieved when using a higher $Cl/Br_2$ molar ratio in the bromination reactor. It also shows that when separating out methane and HBr from the bromination product stream, the synthesis reactor feed rate became nearly independent of the use of $Cl/Br_2$ molar ratio in the upstream bromination reactor. However, in the absence of this step, the synthesis reactor feed increased by 58% from 11,822 to 18,673 kgmol/h, when the $Cl/Br_2$ molar ratio used in the upstream bromination reactor was increased from 2.5 to 5.

TABLE 1

|  |  | $Cl/Br_2$ molar ratio use in bromination reactor | |
|---|---|---|---|
|  |  | 2.5 | 5 |
| $Br_2$ conversion | (%) | 100 | 100 |
| $CH_3Br$ selectivity[1] | (mol %) | 70 | 80 |
| $CH_2Br_2$ selectivity[1] | (mol %) | 25 | 15 |
| Other bromination products selectivity[1] | (mol %) | 5 | 5 |
| Bromination effluent rate | (kgmol/h) | 11,822 | 18,673 |
| Synthesis reactor feed rate without $CH_3Br$ fractionation (comparative) | (kgmol/h) | 11,822 | 18,673 |
| Synthesis reactor feed rate with $CH_3Br$ fractionation | (kgmol/h) | 2,528 | 2,526 |
| Reduction of synthesis reactor feed rate by using $CH_3Br$ fractionation | (%) | 78.6 | 86.5 |

[1]$CH_3Br$ selectivity (mol %) = mole of $CH_3Br$/moles of ($CH_3Br + CH_2Br_2$) + other bromination products) × 100%. Similar definition applies to $CH_2Br_2$ selectivity and other bromination products selectivity.

Example 2

Additional simulations were conducted to further analyze the inclusion of an alkyl bromides fractionation unit in a process for converting natural gas to liquid hydrocarbons via a bromine-based method. 50 MMSCFD of natural gas was fed to the process illustrated by FIG. 4B, but without an alkyl bromides fractionation unit between the bromination reactor and the synthesis reactor. A $Cl/Br_2$ mixture having a $Cl/Br_2$ molar ratio of 2.5 entered a bromination reactor at 150° to 300° C. and 35 Barg and left at 450° C. to 500° C. The fresh natural gas feed entered the cryogenic separation section of the product recovery unit which was also fed by a major stream containing all of the recycle methane routed from the stabilization section of the same unit. The combined feeds to the cryogenic separation section amounted to a rate of 8,716 kgmol/h. In the case of separating Cl/HBr from alkyl bromides by fractionating downstream of the bromination reactor, as illustrated by FIG. 4B, the feed to the cryogenic separation section was reduced by 68.3% to 2,766 kgmol/h.

For comparison, the same 50 MMSCFD of natural gas was a fed to the same process illustrated by FIG. 4B, but using a $Cl/Br_2$ molar ratio of 5 in the bromination reactor. Without using an alkyl bromides fractionation unit between the bromination reactor and the synthesis reactor, the combined feed rates to the cryogenic separation section was 15,832 kgmol/h. When Cl/HBr are separated from the alkyl bromides by fractionating downstream of the bromination reactor, as illustrated by FIG. 4B, the feed to the cryogenic separation section was reduced by 82.5% to 2,766 kgmol/h.

The above results are summarized in Table 2. It shows that when methane and HBr are separated out prior to feeding the bromination product stream to the synthesis reactor, the cryogenic separation section feed rate was independent of the use of $Cl/Br_2$ molar ratio in the upstream bromination reactor. However, in the absence of this step, the synthesis reactor feed increased by 82% from 8,716 to 15,832 kgmol/h, when the $Cl/Br_2$ molar ratio used in the upstream bromination reactor was increased from 2.5 to 5.

TABLE 2

|  |  | $Cl/Br_2$ molar ratio used in bromination reactor | |
|---|---|---|---|
|  |  | 2.5 | 5 |
| Cryogenic separation section feed rate without $CH_3Br$ fractionation (comparative) | (kgmol/h) | 8,716 | 15,832 |
| Cryogenic separation section feed rate with $CH_3Br$ fractionation | (kgmol/h) | 2,766 | 2,766 |
| Reduction of Cryogenic separation section feed by using $CH_3Br$ fractionation | (%) | 68.3 | 82.5 |

Example 3

Additional simulations were conducted to further analyze the inclusion of an alkyl bromides fractionation unit in a process for converting natural gas to liquid hydrocarbons via a bromine-based method. 50 MMSCFD of natural gas comprising 97.1 mol % Cl and 2.9 mol % C2+ hydrocarbon impurities was fed to the process illustrated by FIG. 4B, but without using an alkyl bromides fractionation unit between the bromination reactor and the synthesis reactor. A $Cl/Br_2$ mixture having a $Cl/Br_2$ molar ratio of 2.5 and a C2+ content of less than 1.0 mol % in Cl entered a bromination reactor at 150° to 300° C. and 35 Barg and left at 450° C. to 500° C. The entire bromination product stream was reacted in a synthesis reactor at 34 barg. The resultant synthesis product stream entered the HBr separator to produce a hydrocarbon stream that was substantially HBr-free. This hydrocarbon stream was dehydrated and then fed to the product recovery unit at 30 barg. The natural gas feed (50 MMSCFD) also fed this unit at 30 barg which produced a 8,444 kgmol/h bromination feed gas stream comprising substantially all of the recycle and feed methane with 1.0 mol % C2+ impurity at 8.5 barg and 30° C. The bromination feed gas stream was then compressed by a feed compressor from 8.5 to 35 barg using 11.7 MW power for reuse in the bromination reactor.

For comparison, the same 50 MMSCFD of natural gas was fed to the same process, but using a Cl/Br$_2$ molar ratio of 5 in the bromination reactor. Without using an alkyl bromides fractionation unit between the bromination reactor and the synthesis reactor, the product recovery unit produced a 15,561 kgmol/h feed gas stream comprising substantially all of the recycle and feed methane with 1.0 mol % C2+ impurity at 8.51 barg and 30° C. The feed gas stream was then compressed by a feed plus recycle compressor from 8.5 to 35 barg using 21.5 MW power for reuse in the bromination reactor.

The above results are summarized in Table 3. It shows that using the process scheme illustrated in FIG. 4B, but without an alkyl bromides fractionation unit, the compression power requirement for feeding and recycling alkanes containing as low as 1 mol % C2+ at 35 barg increased by 83.8% from 11.7 to 21.5 MW, when the Cl/Br$_2$ molar ratio used in the upstream bromination reactor increased from 2.5 to 5.

TABLE 3

| | | Cl/Br$_2$ molar ratio used in bromination reactor | |
|---|---|---|---|
| | | 2.5 | 5 |
| Bromination reactor operating pressure | (barg) | 35 | 35 |
| Feed + Recycle Compressor inlet pressure | (barg) | 8.51 | 8.51 |
| Feed + Recycle Compressor duty (comparative) | (MW) | 11.7 | 21.5 |

Example 4

Additional simulations were conducted to further analyze the inclusion of an alkyl bromides fractionation unit in a process for converting natural gas to liquid hydrocarbons via a bromine-based method. 50 MMSCFD of natural gas was fed to a process illustrated by FIG. 4B. A Cl/Br$_2$ mixture having a Cl/Br$_2$ molar ratio of 2.5 and a C2+ content of less than 1.0 mol % in Cl enters a bromination reactor at 150° C. to 300° C. and 35 Barg and leaves at 450° C. to 500° C. Fractionation of the bromination product stream in an alkyl bromides fractionator, as shown in FIG. 4B, produced a gaseous alkane/HBr stream comprising unreacted alkanes and HBr and a liquid alkyl bromides stream. The gaseous alkane/HBr stream entered the second HBr separator at 32 barg to produce a 5,950 kgmol/h recycle gas stream that was substantially free of HBr. This recycle gas stream was then dehydrated and compressed by a recycle compressor from 28.6 barg to 35 barg using 1.0 MW power for reuse in the bromination reactor. The 50 MMSCFD NG fed a product recovery unit at 30 barg which produced 2,520 kgmol/h feed gas stream comprising substantially all of the feed methane with 1.0 mol % C2+ impurity at 14.2 barg and 30° C. The feed gas stream was then compressed by a feed compressor from 14.2 barg to 35 barg using 2.1 MW power to feed the bromination reactor. The total compression power required for sending the feed and the recycle alkanes to the bromination reactor at 35 barg was 3.1 MW.

For comparison, the same 50 MMSCFD of natural gas was fed to the same process described above and shown in FIG. 4B, but using a Cl/Br$_2$ molar ratio of 5 in the bromination reactor. The second HBr separator produced a 13,066 kgmol/h recycle gas stream that was substantially free of HBr and contains less than 1 mol % C2+. This stream was then dehydrated and compressed by a recycle compressor from 28.6 barg to 35 barg using 2.2 MW power for reuse in the bromination reactor. The product recovery unit produced a 2,520 kgmol/h bromination feed gas stream comprising substantially all of the feed methane with 1.0 mol % C2+ impurity at 14.2 barg and 30° C. The bromination feed gas stream was then compressed by a feed alkane compressor from 14.2 to 35 barg using 2.1 MW power to feed the bromination reactor. The total compression power required for sending the feed and the recycle alkanes to the bromination reactor at 35 barg was 4.3 MW.

The above results are summarized in Table 4. It also shows that using the process scheme illustrated in FIG. 4B, the compression power requirement for feeding and recycling methane containing less than 1 mol % C2+ at 35 barg increased from 3.1 to 4.3 MW, when the Cl/Br$_2$ molar ratio used in the upstream bromination reactor increased from 2.5 to 5.

Comparison to Table 3 of Example 3 also shows that when the Cl/Br$_2$ molar ratio used in the upstream bromination reactor was 2.5, separation out of alkanes and HBr prior to feeding the bromination production stream to the synthesis reactor largely reduced the compression power requirement by 73.5% from 11.7 to 3.1 MW for feeding and recycling alkanes containing equal to or less than 1 mol % C2+ at 35 barg to the bromination reactor. When the said Cl/Br$_2$ molar ratio was 5, the said reduction was from 21.5 to 4.3 MW or by 80%.

TABLE 4

| | | Cl/Br$_2$ molar ratio used in bromination reactor | |
|---|---|---|---|
| | | 2.5 | 5 |
| Bromination reactor operating pressure | (barg) | 35 | 35 |
| Recycle compressor inlet pressure | (barg) | 28.6 | 28.6 |
| Recycle compressor duty | (MW) | 1.0 | 2.2 |
| Feed compressor inlet pressure | (barg) | 14.2 | 14.2 |
| Feed compressor duty | (MW) | 2.1 | 2.1 |
| Total compression duty | (MW) | 3.1 | 4.34 |

Example 5

Additional simulations were conducted to further analyze the inclusion of an alkyl bromides fractionation unit in a process for converting natural gas to liquid hydrocarbons via a bromine-based method. 50 MMSCFD of natural gas was fed to the conversion process. A Cl/Br$_2$ mixture having a Cl/Br$_2$ molar ratio of 2.5 entered the bromination reactor at 150° C. to 300° C. and 35 Barg and left at 450° C. to 500° C. The bromination product stream comprising 29 mol % HBr, 50 mol % methane, and 21 mol % Cl bromides fed an alkyl bromides fractionator at a rate of 11,822 kgmol/h. With reference to FIG. 7, this column fractionated the feed into a 9,294 kgmol/h gaseous alkane/HBr stream at 32 barg comprising substantially all of the HBr and methane fed to the fractionator and a 2,528 kgmol/h liquid alkyl bromides stream comprising substantially all of the methyl bromide and heavier bromides fed to the fractionator. The fractionator specifications included 1% HBr recovery in the bottoms and 1 ppmw CH$_3$Br in the overheads. The condenser temperature was −8.6° C. requiring a refrigeration duty of 11 MW. The reboiler temperature was 168° C. requiring a steam duty of 17 MW.

For comparison, 50 MMSCFD of natural gas was fed to the same process described above but using a Cl/$Br_2$ molar ratio of 5. The bromination product stream comprising 17 mol % HBr, 70 mol % methane, and 13 mol % Cl bromides fed an alkyl bromides fractionator at a rate of 18,673 kgmol/h. This column fractionated the feed into a 16,147 kgmol/h gaseous alkane/HBr stream at 32 barg comprising substantially all of the HBr and methane fed to the fractionator and a 2,526 kgmol/h liquid alkyl bromides stream comprising substantially all of the methyl bromide and heavier bromides fed to the fractionator. The same fractionator specifications were used as above. The condenser temperature was −31° C. requiring a refrigeration duty of 11 MW. The reboiler temperature was 160° C. requiring a steam duty of 14 MW.

The above results are summarized in Table 5.

TABLE 5

|  |  | Cl/$Br_2$ molar ratio used in bromination reactor | |
|---|---|---|---|
|  |  | 2.5 | 5 |
| $CH_3Br$ Fractionator feed | (kgmol/h) | 11,822 | 18,673 |
| $CH_3Br$ Fractionator overhead rate | (kgmol/h) | 9,294 | 16,147 |
| $CH_3Br$ Fractionator bottoms rate | (kgmol/h) | 2,528 | 2,526 |
| $CH_3Br$ Fractionator condenser temperature | (° C.) | −8.6 | −31 |
| $CH_3Br$ Fractionator condenser duty | (MW) | 11 | 16 |
| $CH_3Br$ Fractionator reboiler temperature | (° C.) | 168 | 160 |
| $CH_3Br$ Fractionator reboiler duty | (MW) | 17 | 14 |

Certain embodiments of the methods of the invention are described herein. Although major aspects of what is to believed to be the primary chemical reactions involved in the methods are discussed in detail as it is believed that they occur, it should be understood that side reactions may take place. One should not assume that the failure to discuss any particular side reaction herein means that that reaction does not occur. Conversely, those that are discussed should not be considered exhaustive or limiting. Additionally, although figures are provided that schematically show certain aspects of the methods of the present invention, these figures should not be viewed as limiting on any particular method of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed.

What is claimed is:

1. A process comprising:
   reacting at least gaseous alkanes and a halogen to produce at least a halogenation product stream, wherein the halogenation product stream comprise alkyl halides, hydrogen halide, and unreacted alkanes;
   separating the alkyl halides from the hydrogen halides and unreacted alkanes in the halogenation product stream using a fractionator to form at least a gaseous stream and a liquid alkyl halides stream, wherein the gaseous stream comprises the hydrogen halide and the unreacted alkanes, and wherein the liquid alkyl halides stream comprises the alkyl halides, the alkyl halides comprising mono-halogenated alkanes and poly-halogenated alkanes, wherein a reflux condenser of the fractionator generates a reflux stream that is fed into the fractionator;
   recovering at least a portion of the hydrogen halide from the gaseous stream; and
   reacting at least a portion of the alkyl halides from the liquid alkyl halides stream in the presence of a catalyst to produce a synthesis product stream, wherein the synthesis product stream comprises higher molecular weight hydrocarbons and hydrogen halides.

2. The process of claim 1 wherein the halogen comprises bromine.

3. The process of claim 1 wherein the higher molecular weight hydrocarbons comprise hydrocarbons having 5 or more hydrocarbons.

4. The process of claim 1 wherein the separating comprises cooling the halogenation product stream, separating the halogenation product stream into a liquid fractionator feed stream and a gaseous fractionator feed stream, and feeding the liquid fractionator feed stream and the gaseous fractionator feed stream into a fractionator, wherein the gaseous stream and the liquid alkyl halides stream are withdrawn from the fractionator.

5. The process of claim 4 wherein the fractionator operates at a pressure of about 20 bars to about 40 bars.

6. The process of claim 4 further comprising withdrawing a second liquid stream from the fractionator and heating the second liquid stream to a temperature of about 100° C. to about 200° C. in a reboiler.

7. The process of claim 4 further comprising withdrawing an overhead vapor stream from the fractionator and cooling the overhead vapor stream to a temperature greater than about −40° C. in a condenser.

8. The process of claim 7 further comprising cooling the overhead vapor stream against the gaseous stream.

9. The process of claim 4 further comprising cooling the gaseous fractionator feed stream against the gaseous stream.

10. The process of claim 1 further comprising cooling the halogenation product stream against a halogenation feed stream comprising the gaseous alkanes and the halogen from the step of reacting at least gaseous alkanes and a halogen.

11. The process of claim 1 wherein the liquid alkyl halides stream comprises less than 2% by weight of the hydrogen halide from the halogenation product stream.

12. The process of claim 1 wherein the liquid alkyl halides stream comprises less than 1% by weight of the hydrogen halide from the halogenation product stream.

13. The process of claim 1 wherein the unreacted alkanes in the gaseous stream comprises methane and alkanes having 2 or more carbons in an amount of less than 1% by mole.

14. The process of claim 1 wherein the gaseous stream comprises less than 10 ppmw alkyl halides.

15. The process of claim 1 wherein the gaseous stream comprises less than 1 ppmw alkyl halides.

16. The process of claim 1 further comprising recovering at least a portion of the hydrogen halide from the synthesis product stream, wherein recovery of the hydrogen halide from the synthesis product stream occurs in the same unit as the recovery of the hydrogen halide from the gaseous stream.

17. The process of claim 1 further comprising recovering at least a portion of the hydrogen halide from the synthesis product stream, wherein recovery of the hydrogen halide from the synthesis product stream occurs in a hydrogen halide separator, and wherein the recovery of the hydrogen halide from the gaseous stream occurs in a second hydrogen halide separator.

18. The process of claim 17 wherein the second hydrogen halide separator operates at a higher pressure than the hydrogen halide separator.

19. The process of claim 1 wherein the recovering at least a portion of the hydrogen halide from the gaseous stream comprises contacting the gaseous alkane stream with an aqueous stream.

20. The process of claim 1 further comprising reacting at least a portion of the alkyl halides from the liquid alkyl halides stream with light end hydrocarbons to convert at least a portion of the alkyl halides from poly-halogenated alkanes to mono-halogenated alkanes prior to the step of reacting at least a portion of the alkyl halides from the liquid alkyl halides stream in the presence of a catalyst to produce a synthesis product stream.

21. The process of claim 1 wherein the catalyst comprises a synthetic crystalline alumino-silicate catalyst.

22. A process comprising
reacting at least gaseous alkanes and bromine in a bromination reactor to produce at least a bromination product stream, wherein the bromination product stream comprise alkyl bromides, hydrogen bromide, and unreacted alkanes;
separating the alkyl bromides from the hydrogen bromide and the unreacted alkanes in the bromination product stream to form at least a gaseous alkane/HBr stream and a liquid alkyl bromides stream, wherein the gaseous alkane/HBr stream comprises the hydrogen bromide and the unreacted alkanes, and wherein the liquid alkyl bromides stream comprises the alkyl bromides, the alkyl bromides comprising mono-brominated alkanes and poly-brominated alkanes;
reacting at least a portion of the alkyl bromides from the liquid alkyl bromides stream in a synthesis reactor to produce a synthesis product stream, wherein the synthesis product stream comprises higher molecular weight hydrocarbons and hydrogen bromide;
recovering at least a portion of the hydrogen bromide from the synthesis product stream in a hydrogen bromide separator;
providing a natural gas stream;
separating at least the synthesis product stream and the natural gas stream into at least a light ends product stream, a heavy ends product stream, and a feed gas stream, wherein the light ends product stream comprises hydrocarbons having from 2 to 4 carbons, wherein the heavy ends product stream comprises hydrocarbons having 5 or more carbons, and wherein the feed gas stream comprises methane;
compressing the feed gas stream in a feed compressor;
feeding the feed gas stream into the bromination reactor;
generating a recycle alkane stream by recovering at least a portion of the hydrogen bromide from the gaseous alkane/HBr stream in a second hydrogen bromide separator operating at a higher pressure than the hydrogen bromide separator;
compressing the recycle alkane stream in a recycle compressor; and
feeding the recycle alkane stream to the bromination reactor.

23. The process of claim 22 wherein the separating the bromination product stream comprises cooling the bromination product stream, separating the bromination product stream into a liquid fractionator feed stream and a gaseous fractionator stream, and feeding the liquid fractionator feed stream and the gaseous fractionator feed stream into a fractionator, wherein the gaseous alkane stream and the liquid alkyl bromides stream are withdrawn from the fractionator.

24. The process of claim 23 wherein the fractionator operates at a pressure of about 20 bars to about 40 bars.

25. The process of claim 23 further comprising cooling the gaseous fractionator feed stream against the gaseous alkane/HBr stream.

26. The process of claim 22 wherein the liquid alkyl bromides stream comprises less than 2% by weight of the hydrogen bromide from the bromination product stream.

27. The process of claim 22 wherein the gaseous alkane/HBr stream comprises less than 10 mppm alkyl bromides.

28. The process of claim 22 wherein the gaseous alkane/HBr stream comprises less than 1 mppm alkyl bromides.

29. The process of claim 22 wherein the recovering at least a portion of the hydrogen bromide from the gaseous alkane/HBr stream comprises contacting the gaseous alkane/HBr stream with an aqueous stream.

30. The process of claim 22 further comprising reacting at least a portion of the alkyl bromides from the liquid alkyl bromides stream with the light end hydrocarbon stream to convert at least a portion of the alkyl bromides from poly-brominated alkanes to mono-brominated alkanes prior to the step of reacting at least a portion of the alkyl bromides from the liquid alkyl bromides stream in the presence of a catalyst to produce a synthesis product stream.

31. The process of claim 22 further comprising:
reacting at least the light end hydrocarbon stream and bromine to form a brominated stream comprising brominated light end hydrocarbons, hydrogen bromide, and unreacted light end hydrocarbons; and
reacting at least a portion of the brominated light end hydrocarbons in the presence of the catalyst in the synthesis reactor.

32. The process of claim 22 wherein the catalyst comprises a synthetic crystalline alumino-silicate catalyst.

33. The process of claim 23, wherein the step of separating the alkyl bromides comprises: feeding the halogenation product stream into a fractionator having a reboiler and a reflux condenser; partially condensing an overhead vapor stream from the fractionator in the reflux condenser; separating the partially condensed overhead vapor stream into a reflux stream and the gaseous alkane/HBr stream; and conveying the reflux stream into the fractionator.

34. The process of claim 33 further comprising cooling the overhead vapor stream in the reflux condenser to a temperature in a range of about −40° C. to about 0° C., the condenser having an operating pressure of about 20 bars to about 40 bars, and further comprising cooling the overhead vapor stream against the gaseous alkane/HBr stream.

35. The process of claim 1 wherein the step of separating the alkyl halides comprises: feeding the halogenation product stream into the fractionator having a reboiler and the reflux condenser; partially condensing an overhead vapor stream from the fractionator in the reflux condenser; separating the partially condensed overhead vapor stream into the reflux stream and the gaseous stream; and conveying the reflux stream into the fractionator.

* * * * *